US009097646B1

(12) United States Patent
Campbell et al.

(10) Patent No.: US 9,097,646 B1
(45) Date of Patent: Aug. 4, 2015

(54) MODULATED SINE WAVES FOR DIFFERENTIAL ABSORPTION MEASUREMENTS USING A CW LASER SYSTEM

(71) Applicant: The United States of America as represented by the Administrator of the National Aeronautics and Space Administration, Washington, DC (US)

(72) Inventors: Joel F. Campbell, Poquoson, VA (US); Bing Lin, Yorktown, VA (US); Amin R. Nehrir, Yorktown, VA (US)

(73) Assignee: UNITED STATES OF AMERICA AS REPRESENTED BY THE ADMINISTRATOR OF THE NATIONAL AERONAUTICS AND SPACE ADMINISTRATION, Washington, DC (US)

(*) Notice: Subject to any disclaimer, the term of this patent is extended or adjusted under 35 U.S.C. 154(b) by 11 days.

(21) Appl. No.: 14/072,019

(22) Filed: Nov. 5, 2013

Related U.S. Application Data

(63) Continuation-in-part of application No. 13/167,093, filed on Jun. 23, 2011, now Pat. No. 8,605,262.

(60) Provisional application No. 61/357,687, filed on Jun. 23, 2010, provisional application No. 61/862,626, filed on Aug. 6, 2013.

(51) Int. Cl.
*G01C 3/08* (2006.01)
*G01N 21/17* (2006.01)

(52) U.S. Cl.
CPC ................................... *G01N 21/17* (2013.01)

(58) Field of Classification Search
CPC ....... G01S 17/325; G01S 7/491; G01S 17/58; G01S 17/102; G01S 17/36
USPC ................. 356/5.09, 4.09, 5.01, 28.5, 3, 496; 235/414
See application file for complete search history.

(56) References Cited

U.S. PATENT DOCUMENTS 6,157,341 A    12/2000  Silvestrin et al.
6,967,607 B2 * 11/2005  Melanson ..................... 341/143
(Continued)

OTHER PUBLICATIONS

Zahradnik, Pavel; Miroslav Vlcek. "Analytical Design of 2-D Narrow Bandstop FIR Filters". M. Bubak et al. (Eds.): ICCS 2004, LNCS 3039, pp. 56-63, 2004. Springer-Verlag Berlin Heidelberg 2004. http://download.springer.com/static/pdf/223/chp%253A10.
1007%252F978-3-540-25944-2_8.pdf?auth66=1420738373_
7e973eceaba1e682ac9cdd4a7b453760&ext=.pdf.*

(Continued)

*Primary Examiner* — Isam Alsomiri
*Assistant Examiner* — Samantha K Abraham
(74) *Attorney, Agent, or Firm* — Andrea Z. Warmbier

(57) ABSTRACT

A continuous wave Light Detection and Ranging (CW LiDAR) system utilizes two or more laser frequencies and time or range shifted pseudorandom noise (PN) codes to discriminate between the laser frequencies. The performance of these codes can be improved by subtracting out the bias before processing. The CW LiDAR system may be mounted to an artificial satellite orbiting the earth, and the relative strength of the return signal for each frequency can be utilized to determine the concentration of selected gases or other substances in the atmosphere.

28 Claims, 20 Drawing Sheets

(56) References Cited

U.S. PATENT DOCUMENTS

| | | | |
|---|---|---|---|
| 7,359,057 B2 | 4/2008 | Schwiesow | |
| 7,361,922 B2 | 4/2008 | Kameyama et al. | |
| 7,616,888 B2 | 11/2009 | Mendenhall et al. | |
| 7,995,917 B2 | 8/2011 | Mendenhall et al. | |
| 2007/0008534 A1 | 1/2007 | Lo et al. | |
| 2009/0153394 A1* | 6/2009 | Navarro et al. | 342/174 |
| 2010/0208231 A1 | 8/2010 | Murai | |

OTHER PUBLICATIONS

WolframMathWorld. "Jacobi Elliptic Functions." http://mathworld.wolfram.com/JacobiEllipticFunctions.html, May 13, 2015.*

WolframResearch. "Introduction to the incomplete elliptic integrals." http://functions.wolfram.com/EllipticIntegrals/EllipticPi3/introductions/IncompleteEllipticIntegrals/ShowAll.html, 2015.*

Snape, Jamie. "Applications of Elliptic Functions in Classical and Algebraic Geometry." Dissertation, University of Durham, Durham, UK, 2004. https://wwwx.cs.unc.edu/~snape/publications/mmath/ and https://wwwx.cs.unc.edu/~snape/publications/mmath/dissertation.pdf.*

NRC, "Earth Science and Applications from Space: National Imperatives for the Next Decade and Beyond," The National Academies Press, 2007, pp. 1-16, 27-60, 79-140, 152-216 and 423-426, Washington, D.C.

Koch, Grady J. et al., "Coherent Differential Absorption Lidar Measurements of CO2," Applied Optics, Sep. 10, 2004, pp. 5092-5099, vol. 43, No. 26.

Abshire, James B. et al., "Pulsed Airborne Lidar Measurements of Atmospheric CO2 Column Absorption," 8th International Carbon Dioxide Conference, ICDC8, Sep. 13-19, 2009, pp. 770-783, vol. 62, Tellus, B. Germany.

Kamayama, Shumpei et al., "Feasibility Study on 1.6 um Continuous-wave Modulation Laser Absorption Spectrometer System for Measurement of global CO2 Concentration from a Satellite," Applied Optics, May 10, 2011, pp. 2055-2068, vol. 50, No. 14.

Campbell, Joel F. et al., "Pseudorandom Noise Code-based Technique for Thin-cloud Discrimination with CO2 and O2 absorption Measurements," Optical Engineering, Dec. 2011, pp. 126002-1-126002-8, vol. 50, No. 12.

Campbell, Joel F. et al., "A Low Cost Remote Sensing System Using PC and Stereo Equipment," Am. J. Phys., Dec. 2011, pp. 1240-1245, vol. 79, No. 12.

Agishev, R. et al., "Atmospheric CW-FM-LD-RR Ladar for Trace-constituent Detection: A Concept Development," Appl. Phy. B, 2005, pp. 695-703, vol. 81.

Batet, Oscar et al., "Intensity-modulated Linear-frequency-modulated Continuous-wave Lidar for Distributed Media: Fundamentals of Technique," Jun. 10, 2010, pp. 3369-3379, vol. 49, No, 17.

Imaki, Masaharu et al., "Laser Absorption Spectrometer Using Frequency Chirped Intensity Modulation at 1.57 um Wavelength for CO2 Measurement," Optics Letters, Jul. 1, 2012, pp. 2688-2690, vol. 37, No. 13.

Browell, Edward V. et, el., Airborne Laser CO2 Column Measurements: Evaluation of Precision and Accuracy Under Wide Range of Conditions, Presented at Fall AGU Meeting, Dec. 5-9, 2011, pp. 1-17, San Francisco, CA.

Browell, Edward V. et al., "Airborne Validation of Laser CO2 and O2 Column Measurements," 16th Symposium on Meteorological Observation and Instrumentation, 92nd AMS Annual Meeting, Jan. 22-26, 2012, New Orleans, LA.

Dobler, Jeremy T. et al., "Atmospheric CO2 Column Measurements with an Airborne Intensity-modulated Continuous Wave 1.57 um Fiber Laser Lidar," Applied Optics, Apr. 20, 2013, pp. 2874-2892, vol. 52, No. 12.

Chen, Songsheng et al., "Digital Lock-in Detection for Multiple-frequency Intensity-modulated Continuous Wave Lidar," Jun. 25-29, 2012, 26th International Laser Radar Conference, SIP-38, Port Heli, Greece.

Dobbs, Michael et al., "Matched Filter Enhanced Fiber-based Lidar for Earth, Weather and Exploration", NASA ESTO Conference, Jun. 2006, pp. 1-6.

Dobbs, Michael et al., "A Modulated CW Fiber Laser-Lidar Suite for the ASCENDS Mission," Proc. 24th International Laser Radar Conference, Jul. 24-29, 2008, Boulder, CO.

Dobler, Jeremy T. et al., "Advancements in a Multifunctional Fiber Laser Lidar for Measuring Atmospheric CO2 and O2," 16th Symposium on Meteorological Observation and Instrumentation, 92nd AMS Annual Meeting, Jan. 22-26, 2012, New Orleans, LA.

Campbell, Joel F., "Nonlinear Swept Frequency Technique for CO2 Measurements Using a CW Laser System," Applied Optics, May 1, 2013, pp. 3100-3107, vol. 52, No. 13.

Campbell, Joel, "Synthetic Quadrature Phase Detector/demodulator for Fourier Transform Spectrometers," Applied Optics, Dec. 20, 2008, pp. 6889-6894, vol. 47, No. 36.

Skinner, B. J. et al., "Matched FSK/PSK Radar," IEEE Proceedings, 1994 National Radar Conference, Mar. 1994, pp. 251-255. Atlanta, GA.

Freeman. J. et al., "Gain Modulation Response of Erbium-Doped Fiber Amplidiers," IEEE Photonics Technology Letters, Feb. 1993, pp. 224-226, vol. 5, No. 2.

Murota, Kazuaki et al., "GMSK Modulation for Digital Mobile Radio Telephony," IEEE Transactions on Communications, Jul. 1981, pp. 1044-1050, vol. COM-29, No. 7.

Whittaker, E.T. et al., "A Course of Modern Analysis" 1965, p. 462, Cambridge University Press, 4th Edition, Cambridge, UK.

Campbell, Joel, "The SMM Model as a Boundary Value Problem Using the Discrete Diffusion Equation," Theor. Popul. Biol., 2007, pp. 539-546, vol. 72, Issue 4.

Campbell, Joel, "Ground State Energy for the Hartree-Fock Equations with Dirichlet Boundary Conditions," J. Math. Phys., Apr. 1994, pp. 1471-1486, vol. 35, No. 4.

Benedetto, John J. et al., "Sampling Multipliers and the Poisson Summation Formula," J. Fourier Anal. Appl. Nov. 5, 1997, pp. 505-523, vol. 3, No. 5.

Kameyama, Shupe et al., "Performance Improvement and Analysis of a 1.6 um Continous-wave modulation Laser Absorption Spectrometer System for CO2 Sensing," Applied Optics, Apr. 10, 2011, pp. 1560-1569, vol. 50, No. 11.

Kameyama, Shupei, et al., "Development of 1.6 um Continuous-wave Modulation Hard-target Differential Absorption Lida System for CO2 Sending" Optics Letters, May 15, 2009, pp. 1513-1515, vol. 34, No. 10.

Takeuchi, N. et al., "Random Modulation CW Lidar," Applied Optics, May 1, 1983, pp. 1382-1386, vol. 22, No. 9.

Rybaltowski, Adam et al., "Signal-to-noise Ratio in Direct-detection Mid-infrared Random-Modulation Continuous-Wave Lidar in the Presence of Colored Additive Noise," Optics Express, Oct. 8, 2001, pp. 386-399, vol. 9, No. 8.

Rybaltowski, Adam et al., "New Modulation Sequence for Random-Modulation Continuous-Wave Lidar," Proceedings of SPIE, 2002, pp. 216-223, vol. 4484.

Rybaltowski, Adam et al., "Figure of Merit and Fundamental Range Limitations in Surface Sensing Direct- detection Mid-infrared Random-Modulation Continuous-Wave Lidar," Proceedings of SPIE, 2002, pp. 32-36, vol. 4546.

Rybaltowski, Adam et al., "Superior Signal-to-noise Ratio of a New AA1 Sequence for Random-modulation Continuous-wave Lidar," Optics Letters, Aug. 1, 2004, pp. 1709-1711, vol. 29, No. 15.

Takeuchi, Nobuo et al., "Diode-laser Random-modulation CW Lidar," Applied Optics, Jan. 1, 1986, pp. 63-57, vol. 25, No. 1.

Sophocles J. Orfanidis, Lecture Notes on Elliptic Filter Design, Nov. 20, 2006, pp. 1-42, Rutgers University.

A Raouf Chouikha, On Properties of Elliptic Jacobi Functions and Applications, Journal of Nonlinear Mathematical Physics, 2005, pp. 162-169, 12:2.

Joel F. Campbell et al., "Advanced sine wave modulation of continuous wave laser system for atmospheric CO2 differential absorption measurements," Applied Optics, 2014, pp. 816-829, vol. 53, Issue 5.

* cited by examiner

MODULATED SINE WAVES FOR DIFFERENTIAL ABSORPTION MEASUREMENTS USING A CW LASER SYSTEM

CROSS-REFERENCE TO RELATED PATENT APPLICATIONS

This application claims the benefit of priority to and is a continuation-in-part of U.S. patent application Ser. No. 13/167,093, filed on Jun. 23, 2011, which claims the benefit of priority to U.S. Provisional Patent Application Ser. No. 61/357,687, filed on Jun. 23, 2010. This application also claims the benefit of priority to U.S. Provisional Patent Application Ser. No. 61/862,626, filed on Aug. 6, 2013. The contents of the foregoing applications are hereby incorporated by reference in their entirety.

STATEMENT REGARDING FEDERALLY SPONSORED RESEARCH OR DEVELOPMENT

The invention was made by employees of the United States Government and may be manufactured and used by or for the Government of the United States of America for governmental purposes without the payment of any royalties thereon or therefore.

FIELD OF THE INVENTION

The present invention relates generally to range detection and differential absorption utilizing Light Detection And Ranging (LiDAR), radar, sonar, or other signal.

BACKGROUND OF THE INVENTION

The U.S. National Research Council's report entitled Earth Science and Applications from Space: National Imperatives for the Next Decade and Beyond identified the need for a middle-term space mission of ASCENDS (NRC, "Earth Science and Applications from Space: National Imperatives for the Next Decade and Beyond," The National Academies Press, Washington, D.C., 2007.) The primary objective of the ASCENDS mission is to make $CO_2$ column mixing ratio measurements during the day and night over all latitudes and all seasons and in the presence of thin or scattered clouds. These measurements would be used to significantly reduce the uncertainties in global estimates of $CO_2$ sources and sinks, to provide an increased understanding of the connection between climate and atmospheric $CO_2$, to improve climate models, and to close the carbon budget for improved forecasting and policy decisions. (NRC, "Earth Science and Applications from Space: National Imperatives for the Next Decade and Beyond," The National Academies Press, Washington, D.C., 2007.)

The ASCENDS mission requires an active sensor that has the needed $CO_2$ column measurement precision from space to determine the global variability of $CO_2$ in the troposphere and thereby determine $CO_2$ sources and sinks at the surface. The critical component in the ASCENDS mission is the Laser Absorption Spectrometer (LAS) for $CO_2$ column measurements with weighting towards the mid to lower troposphere using Integrated Path Differential Absorption (IPDA) technique.

IPDA lidar systems measure the difference of the total gas absorption along the path length between two or more laser wavelengths in the path of the laser to a target. For the earth's climate system, there are large changes in the atmospheric variables such as pressure and temperature profiles, clouds, aerosols, and the profiles of water vapor and other absorbing gases from local spot to global scales. Also, the surface reflectance varies with many factors and variables such as surface type, roughness, slope, vegetation, and soil moisture. The variations in these atmospheric and surface factors and variables would generate large changes in received lidar powers from the surface or other targets, which would introduce huge problems in determination of $CO_2$ column amounts when individual lidar wavelengths are investigated. The advantage of IPDA LAS system is that the strong effects of the variations in atmospheric states and surface reflection on lidar return powers would be eliminated from the ratio of received lidar powers of two close wavelengths. All the influences on the lidar power from these environmental variables are the same for the two or more close wavelengths. The ratio removes all environmental effects except the differential absorption optical depth at the studied LAS wavelengths. Thus, high accuracy of $CO_2$ column measurements (within 1 ppm) can be achieved from the $CO_2$ differential optical depth.

Basic $CO_2$ IPDA LAS measurement approaches include pulsed (Grady J. Koch, Bruce W Barnes, Mulugeta Petros, Jeffrey Y Beyon, Farzin Amzajerdian, Jirong Yu, Richard E Davis, Syed Ismail, Stephanie Vay, Michael J Kavaya, Upendra N Singh. "Coherent Differential Absorption Lidar Measurements of CO2," Applied Optics, Vol. 43 Issue 26, pp. 5092-5099 (2004) doi: 10.1364/AO.43.005092) and (James B. Abshire, Haris Riris, Graham R. Allan, Clark J. Weaver, Jianping Mao, Xiaoli Sun, William E. Hasselbrack, S. Randolph Kawa "Pulsed airborne lidar measurements of atmospheric $CO_2$ column absorption," Presented at the 8th international carbon dioxide conference, ICDC8, in Jena Germany 13-19 Sep. 2009, Tellus B, 62: 770-783, doi: 10.1111/j.1600 0889.2010.00502.x) and CW systems. Direct detection pulsed systems use a technique where measurements for each wavelength are done sequentially through separate columns. This works well but errors can occur if there are differences in reflectivity and solar background radiation from shot to shot and one wavelength to the next. Also, the atmospheric air mass measured for pulse systems is different from one wavelength pulse to other wavelength pulses. The CW approach, however, transmits lidar powers of different wavelengths in the same aligned laser beam, fundamentally senses the same column of atmosphere and spot of surface, and thus, removes the potential errors for pulse systems. Within the CW approach, IM techniques are used to separate the signals from different wavelengths, provide ranging capability, and discriminate surface returns from multiple other returns such as those of thin clouds, for instance. They are also useful for separating the laser signals from background solar returns, which occurs in a natural way through the matched filter processing techniques used. Potential IM-CW techniques include pn code CW (Joel F. Campbell, Narasimha S. Prasad, Michael A. Flood "Pseudorandom noise code-based technique for thin-cloud discrimination with $CO_2$ and $O_2$ absorption measurements," Opt. Eng. 50(12), 126002 (Nov. 18, 2011), doi:10.1117/1.3658758) and (Joel F. Campbell, Michael A. Flood, Narasimha S. Prasad, and Wade D. Hodson "A low cost remote sensing system using PC and stereo equipment," American Journal of Physics, Vol. 79, Issue 12, pp. 1240, December 2011), linear swept sine wave CW (R. Agishev, B. Gross, F. Moshary, A. Gilerson, and S. Ahmed "Atmospheric CW-FM-LD-RR ladar for trace-constituent detection: a concept development," Appl. Phys. B 81, 695-703(2005), doi: 10.1007/s00340-005-1919-x), (Oscar Batet, Federico Dios, Adolfo Comeron, and Ravil Agishev "Intensity-modulated linear-frequency-modulated continuous-wave lidar for distributed media:fundamentals of technique," Applied Optics, Vol. 49, No. 17, pp. 3369-3379, 10 Jun. 2010 doi: 10.1364/AO.49.003369), (Masaharu Imaki, Shumpei Kameyama, Yoshihito Hirano, Shinichi Ueno, Daisuke Sakaizawa, Shuji Kawakami, Masakatsu Nakajima "Laser absorption spectrometer using frequency chirped intensity modulation at 1.57 μm wavelength for CO2 measurement," Optics Letters, Vol. 37, No. 13, pp. 2688-2690, 1 Jul. 2012 doi: 10.1364/OL.37.002688), (Edward V. Browell, J. T. Dobler, S. A. Kooi, M. A. Fenn, Y. Choi, S. A. Vay, F. W. Harrison, B. Moore III "Airborne laser CO2 column measurements: Evaluation of precision and accuracy under wide range of conditions," Presented at Fall AGU Meeting, San Francisco, Calif., 5-9 Dec. 2011) (Edward V. Browell, J. T. Dobler, S. A. Kooi, M. A. Fenn, Y. Choi, S. A. Vay, F. W. Harrison, B. Moore III "Airborne validation of laser CO2 and 02 column measurements," Proceedings, 16th Symposium on Meteorological Observation and Instrumentation, 92nd AMS Annual Meeting, New Orleans, La., 22-26 Jan. 2012. https://ams.confex.com/ams/92Annual/webprogram/Paper197980.html), and (Jeremy T. Dobler, F. Wallace Harrison, Edward V. Browell, Bing Lin, Doug McGregor, Susan Kooi, Yonghoon Choi, and Syed Ismail "Atmospheric CO2 column measurements with an airborne intensity-modulated continuous wave 1.57 μm fiber laser lidar," Applied Optics, Vol. 52, Issue 12, pp. 2874-2892 (2013)), unswept sine wave CW (Songsheng Chen, Yingxin Bai, Larry B. Petway, Byron L. Meadows, Joel F. Campbell, Fenton W. Harrison, Edward V. Browell "Digital Lock-in detection for multiple-frequency intensity-modulated continuous wave lidar," 26th International Laser Radar Conference, S1P-38, Porto Heli, Greece, Porto Heli, Greece, 25-29 Jun. 2012), (Shumpei Kameyama, Masaharu Imaki, Yoshihito Hirano, Shinichi Ueno, Shuji Kawakami, Daisuke Sakaizawa, Toshiyoshi Kimura, Masakatsu Nakajima "Feasibility study on 1.6 mm continuous-wave modulation laser absorption spectrometer system for measurement of global CO2 concentration from a satellite," Applied Optics, Vol. 50, No. 14, pp. 2055-2068 (2011), doi: 10.1364/AO.50.002055) (Michael Dobbs, Jeff Pruitt, Nathan Blume, David Gregory, William Sharp "Matched Filter Enhanced Fiber-based Lidar for Earth, Weather and Exploration," NASA ESTO conference, June 2006 http://esto.nasa.gov/conferences/estc2006/papers/b4p3.pdf). (Dobbs, M. E., J. Dobler, M. Braun, D. McGregor, J. Overbeck, B. Moore III, E. V. Browell, and T. Zaccheo "A Modulated CW Fiber Laser-Lidar Suite for the ASCENDS Mission," Proc. 24th International Laser Radar Conference, Boulder, Colo., 24-29 Jul. 2008). and (Jeremy T. Dobler, ITT Exelis, Fort Wayne, Ind.; and J. Nagel, V. L. Temyanko, T. S. Zaccheo, E. V. Browell, F. W. Harrison, and S. A. Kooi "Advancements in a multifunctional fiber laser lidar for measuring atmospheric CO2 and O2," Proceedings, 16th Symposium on Meteorological Observation and Instrumentation, 92nd AMS Annual Meeting New Orleans, La., 22-26 Jan. 2012. https://ams.confex.com/ams/92Annual/webprogram/Paper202790.html), non-linear swept sine wave CW (Joel F. Campbell "Nonlinear swept frequency technique for CO2 measurements using a CW laser system," Applied Optics, Vol. 52, Issue 13, pp. 3100-3107 (2013)), and other similar techniques. The baseline technique used by NASA Langley Research Center in partnership with ITT Exelis for the ASCENDS mission is linear swept frequency CW (Jeremy T. Dobler, F. Wallace Harrison, Edward V. Browell, Bing Lin, Doug McGregor, Susan Kooi, Yonghoon Choi, and Syed Ismail "Atmospheric CO2 column measurements with an airborne intensity-modulated continuous wave 1.57 μm fiber laser lidar," Applied Optics, Vol. 52, Issue 12, pp. 2874-2892 (2013)). Experiments have demonstrated the utility of this technique for both range and CO2 column absorption measurements. An advantage of this technique is that by simultaneously transmitting orthogonal online and offline signals together through a single column of atmosphere, one may make a simultaneous online/offline lidar return power measurement, thereby minimizing error caused by variations in surface reflectivity and reflected solar background radiation.

One potential issue with some modulation techniques, such as linear swept frequency, is the potential for side lobes, which could introduce small bias errors when intermediate scatterers are close to measurement targets. This is an advantage of digital techniques such as pseudorandom-noise (PN) codes and non-linear frequency modulation. A known technique uses a pure maximum length (ML) sequence with time shifting to separate channels (Joel F. Campbell, Narasimha S. Prasad, Michael A. Flood "Pseudorandom noise code-based technique for thin-cloud discrimination with CO2 and O2 absorption measurements," Opt. Eng. 50(12), 126002 (Nov. 18, 2011), doi:10.1117/1.3658758). This technique may have the advantage of eliminating the side lobe issue for certain hardware configurations in LAS systems, while allowing for multiple channels that share the same bandwidth. Additionally, the time shifting approach makes the data processing of multi-channel laser returns very simple since one only needs to perform a single matched filter correlation for all channels instead a separate matched filter correlation for each channel. One potential disadvantage with this technique is that not all hardware has a suitable low frequency response, which applies to the transmitter as well as the receiver. Since a ML sequence has a main power band at zero frequency, using that technique in such hardware will filter out the main power band and ruin the autocorrelation properties, which can result in non-orthogonality in a time shifted multi-channel configuration. This problem could be solved by putting the PN code on a carrier, performing amplitude demodulation, and conducting matched filter correlation with the reference PN code to obtain the range capability. A low cost demonstration of this was implemented using Hilbert Transforms forms for amplitude demodulation. That system had better autocorrelation properties but still exhibited minor artifacts and the demodulated PN code exhibited minor distortions and ringing (Joel F. Campbell, Michael A. Flood, Narasimha S. Prasad, and Wade D. Hodson "A low cost remote sensing system using PC and stereo equipment," American Journal of Physics, Vol. 79, Issue 12, pp. 1240, December 2011).

BRIEF SUMMARY OF THE INVENTION

A differential absorption measurement according to the present invention utilizes a two-wavelength approach, which uses one laser with the wavelength tuned to the gas absorption line (on-line), and the other tuned away from that absorption line (off-line). The differential absorption optical depth for the $CO_2$ column may be derived from the ratio of the received optical power from each wavelength.

These and other features, advantages, and objects of the present invention will be further understood and appreciated by those skilled in the art by reference to the following specification, claims, and appended drawings.

DETAILED DESCRIPTION OF PREFERRED EMBODIMENTS

For purposes of description herein, terms such as "upper," "lower," "right," "left," "rear," "front," "vertical," "horizontal," and derivatives may be utilized. However, it is to be understood that the invention may assume various alternative orientations and step sequences, except where expressly specified to the contrary. It is also to be understood that the specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

In atmospheric science it is useful to use PN codes at multiple laser wavelengths in order to measure absorption at specific ranges in order to, for example, discriminate the return of a cloud from the ground.

One aspect of the present invention is the use of time shifted PN codes for continuous wave (CW) LiDAR. In order to frame the requirements for use of time shifted PN codes, it is helpful to define the resolution and range in terms of known quantities.

The resolution is given by:

$$res = \frac{c}{2 * bitrate}, \tag{1.0}$$

where c is the speed of light and bitrate is the bitrate of the PN code. In our reference system res=3*10^8 meters/sec/(2*50000/sec)=3000 meters. The range is:

$$range = N * res. \tag{2.0}$$

For instance with a PN code with a length of 256 the range would be 768 km, which is all the range that would be needed for a typical satellite-based LiDAR system. However, as discussed in more detail below, there are advantages to making the code longer.

Figure 1:
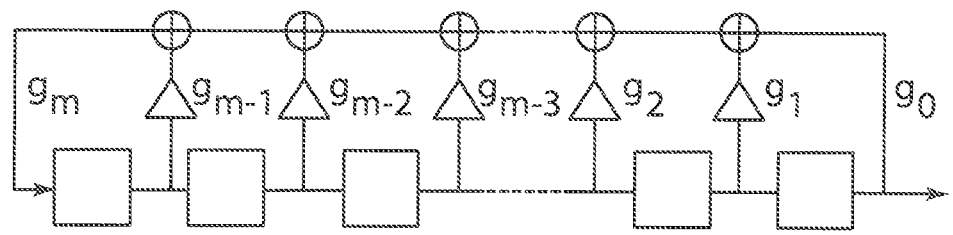
FIG. 1 is a partially fragmentary diagram of a shift register representation for generating m-sequence codes.

One known PN code is the m-sequence. The m-sequence is also the basis of many other PN codes. The m-sequences are advantageous because they have very good autocorrelation properties. M-sequences can be represented in a number of different ways. One known method utilizes linear feedback shift registers. An example of this implementation is shown in FIG. 1. In this arrangement, all additions are done using modulo 2 additions.

M-sequences may also be represented using a generator polynomial:

$$G = g_m x^m + g_{m-1} x^{m-1} + g_{m-2} x^{m-2} + \ldots + g_2 x^2 + g_1 x^1 + g_0. \quad (3.0)$$

Here the g's can be 1 or 0 and the sums are done using modulo two addition. However, $g_m = g_0 = 1$.

These sequences are $2^m - 1$ in length and only specific polynomials can be used for a particular length. For m=8 which corresponds to a code length of $2^8 - 1 = 255$ an allowed polynomial is:

$$G = x^8 + x^6 + x^5 + x^2 + 1. \quad (4.0)$$

In order to generate the individual bits, this can be represented by the recursion relation:

$$pn_{n+8} = pn_n \oplus pn_{n+2} \oplus pn_{n+5} \oplus pn_{n+6} \quad (5.0)$$

For the initial values of $pn_0$-$pn_7$ any sequence of 0's and 1's can be chosen as the seed as long as they are not all 0. For a seed of (1,0,1,0,1,1,1) we generate the sequence: (1, 0, 1, 0, 1, 1, 1, 1, 0, 0, 1, 1, 1, 0, 1, 0, 0, 0, 0, 1, 0, 1, 0, 1, 1, 0, 0, 1, 0, 1, 0, 0, 0, 1, 0, 1, 1, 0, 0, 0, 0, 0, 1, 1, 0, 0, 1, 0, 0, 0, 1, 1, 0, 0, 0, 0, 0, 1, 1, 0, 0, 0, 0, 1, 1, 0, 1, 0, 1, 1, 1, 1, 1, 1, 0, 1, 1, 1, 0, 0, 0, 0, 1, 0, 0, 0, 0, 0, 1, 0, 0, 1, 0, 1, 0, 1, 0, 1, 1, 1, 1, 1, 0, 0, 0, 0, 0, 0, 1, 1, 1, 0, 1, 1, 0, 0, 1, 1, 1, 0, 1, 0, 1, 0, 1, 0, 1, 0, 0, 0, 0, 0, 0, 0, 1, 0, 1, 1, 1, 0, 1, 1, 0, 1, 0, 1, 0, 1, 1, 1, 1, 0, 1, 1, 1, 1, 1, 0, 1, 1, 1, 0, 0, 0, 0, 0, 1, 1, 1, 1, 1, 1, 0, 1, 1, 1, 0, 1, 0, 1, 1, 0, 1, 1, 1, 0, 1, 1, 1, 0, 0, 0, 1, 1, 1, 1, 0, 0, 1, 0, 1, 0, 0, 1, 1, 1, 1, 0, 1, 0, 1, 1, 1, 0, 1, 1, 1, 1, 1, 0, 0, 1, 0, 1, 0, 0, 0, 0, 1, 1, 0, 1, 1, 1, 0, 1, 0, 1, 1, 0, 1, 0, 0, 1, 1, 0, 0, 1, 1, 1, 0, 1, 0, 1, 0, 1, 1, 1, 1, 1, 0, 0, 0, 1, 1, 1, 1, 0, 0, 1, 1, 0, 0, 0, 1, 0, 0, 0, 1, 1, 1, 1, 0, 1, 0, 0, 0, 1, 0, 1, 1, 0, 1, 0, 0, 1, 1, 1, 1, 1, 0, 1, 1, 0, 0, 0, 1, 0, 0, 1, 1, 1, 0, 1, 0, 0, 0, 1, 0, 0, 0, 1, 0, 0, 1, 0, 1, 1, 1, 1, 0, 1, 0, 0, 0, 1, 1, 0, 0, 1, 1, 0, 0, 0, 0, 1, 1, 1, 0, 0, 1, 0, 0, 0, 1, 1, 1, 1, 1, 0, 1, 0, 0, 0, 1, 0, 0, 1, 0, 1, 0, 1, 1, 1, 1, 1, 1)

Figure 2:
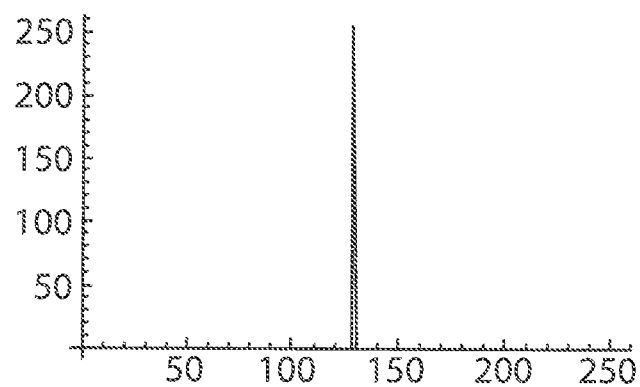
FIG. 2 is a graph showing the result of cross correlation of code and shifted code computed with a fast Fourier transform for a single channel system.

The m-sequence codes have very good autocorrelation properties. The cross correlation between itself and a shifted version of itself is N when they are in sync and −1 if they are not, where N is the length of the code. It is also understood the codes are AC coupled before any correlation is done by changing all 0's in the code by −1. There are a number of ways of computing the correlation. One is by computing a table of:

$$R(ref, \text{data}) = \quad (6.0)$$

$$\frac{1}{N} \sum_{m=0}^{N-1} ref^*(m) \, \text{data} \, (m+n) = DFT^{-1}(DFT^*(ref)DFT(\text{data})),$$

where the * indicates the complex conjugate and DFT is the digital Fourier transform, which may be implemented as a fast Fourier transform (FFT). Although one may compute the sum directly, it requires something on the order of $N^2$ steps. Fast Fourier transforms are generally faster. This is because they only take something on the order of N log N steps. As an example, the case in the previous section can be taken, and the cross correlation between it and a code shifted 128 places to the right can be computed. FIG. 2 shows the results of cross correlation of code and shifted code computed with FFT.

As a simulation, the return signal from a hard target may be represented as a combination of the delayed PN code in combination with noise. If M is the number of samples per bit of a Data Acquisition System (DAQ), and N is the length of the code, the strength of the signal after cross correlation will be N*M when the return signal and PN code are in sync, and −M when they are out of sync in the absence of noise.

Figure 3:
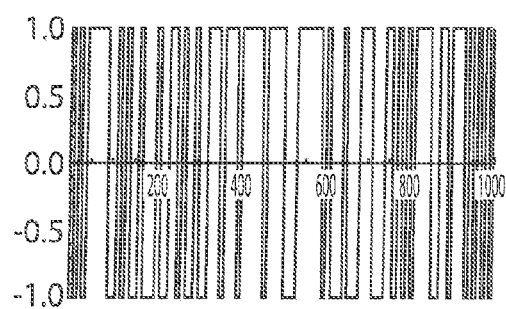
FIG. 3 is a graph of a return signal for a single channel system after subtracting noise.
Figure 4:
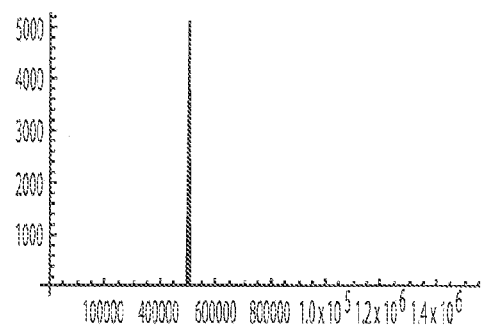
FIG. 4 is a graph of the return signal of FIG. 3 after correlation.
Figure 5:
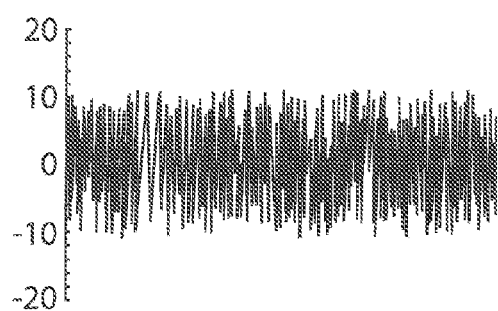
FIG. 5 is a graph of a return signal for a single channel system with 10× noise before correlation.
Figure 6:
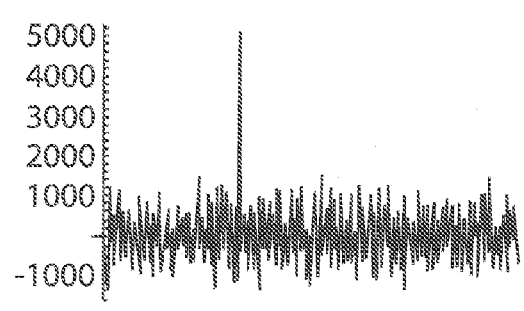
FIG. 6 is a graph showing a return signal for a single channel system with 10× noise after correlation.

As an example, 1 can be chosen as the amplitude of the return signal in combination with random noise 10 times that level. This example also utilizes a code that is 511 bits long, a bitrate of 50000 bits/sec, and a DAQ sample rate of 500000 samples/sec. This gives a resolution of 3 km and a range of 1533 km. A code with the generating function $G = x^9 + x^7 + x^5 + x^2 + 1$ and a seed of (1,0,1,0,1,1,1,1,1) is also chosen, as is a delay corresponding to 500 km. FIG. 3 shows the return signal for this example of a single channel system in absence of noise before correlation, and FIG. 4 shows the return signal after correlation for this example of a single channel system. FIG. 5 shows the same signal buried in noise that is 10 times the amplitude of the signal before correlation, and FIG. 6 shows the signal of FIG. 5 after correlation. The signal can be readily picked out after correlation.

The signal to noise ratio can be estimated. For purposes of discussion, white noise is first considered. It is possible to estimate the signal to noise ratio improvement before and after correlation. In this situation a DAQ samples the signal at:

$$M = \frac{samplerate}{bitrate} \quad (8.0)$$

samples per bit, where samplerate is the DAQ sample rate and bitrate is the PN code bit rate. This increases the apparent code length by M, which must be taken into account when applying the correlation calculation and the new code length becomes MN samples long.

In general, white noise may be computed as a series of pseudorandom numbers ranging from −1 to 1. To generate pink noise, white noise can be filtered with an FFT filter using 1/Sqrt[f] as a filter kernel, thereby giving it a power spectrum of 1/f. For atmospheric species detection it may be advantageous to be able to decode multiple channels. M-sequences (for example) may be utilized to construct a system with two or more channels. Since m-sequences have very good autocorrelation properties, shifted versions of them cross correlate well except for a small CD component where they are uncorrelated and a large spike where they correlate.

Also, if the LiDAR system is mounted to an artificial satellite and the LiDAR system is directed down from space, there will be a final hard target (the ground) below which there will be no further returns possible. If it is known that there will be no further returns past a certain distance, the LiDAR system can be sized with twice the range that is otherwise needed, and that further range can be used to add a second shifted code that is shifted by half the doubled range. To get twice the range a PN code twice as long is used, while maintaining the same code bit rate. As long as there are no returns beyond the half range there will be no interference between the channels. The first half of the autocorrelation gives the range information for the first unshifted channel, and the second half of the autocorrelation gives the range information for the shifted second channel. The autocorrelation for both channels can be done in a single step utilizing, for example, software that has been configured to perform the necessary calculations. By doubling the length of the code the signal to noise ratio (snr) is increased. In general, the code can be as long as needed to add the desired number of channels.

Figure 7:
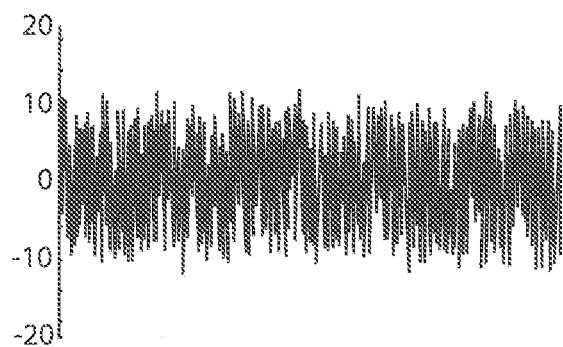
FIG. 7 is a graph of a return signal utilizing two codes in a double ranged system with two channels before correlation.
Figure 8:
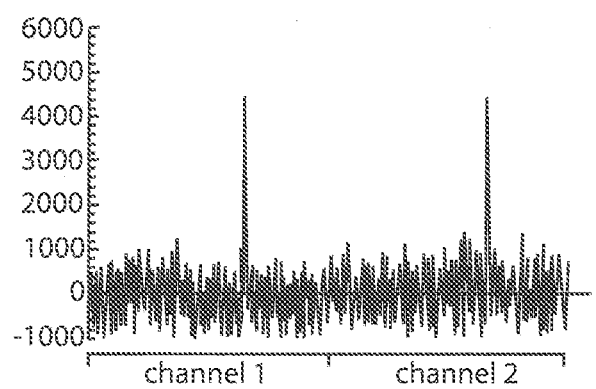
FIG. 8 is a graph of an example of a return signal utilizing two codes in a double ranged system with two channels after correlation.

FIGS. 7 and 8 show an example of using two codes in a double ranged system with two channels before (FIG. 7) and after (FIG. 8) correlation. The example of FIGS. 7 and 8 utilizes a code length of 511 with a sample rate of 500000 samples/sec and a code bit rate of 50000 bits/sec. This gives a total range of 511*3*10^5/(2*50000)=1533 km. A code with the generating function $G=x^9+x^7+x^5+x^2+1$, a seed of (1,0,1,0,1,1,1,1,1) and a shifted version of that code shifted 256 places to the right was used to generate the code. The result of this and 10× noise is show in FIG. 7. This example is similar to the example above (FIGS. 2-6), except that two channels are utilized.

In summary, two or more channels and two or more orthogonal PN codes are utilized, wherein each PN code is shifted in time. Two or more PN codes may be used on a single (or no) carrier. The shifting of the codes may be done such that there is equal spacing. The spacing between the time shifted sequences depends on the range. The minimum distance in bits must be:

$$n > \frac{2*br*R}{c} \qquad (9.0)$$

where n is the distance in bits, br is the bitrate, R is the maximum range, and c is the speed of light. Also, a code must be selected that is at least as long as the sum of all the distances.

For instance, with two codes of length 511, the second is shifted to the right 256 places with respect to the first code. The shifting is done in such a way that as the end of the code is shifted past the boundary it wraps to the beginning. The maximum distance to the farthest target shall be 255 in that case. With four codes of length 511, each is shifted 128 places to the right of the preceding code. The maximum distance to the target in that case would be 127. In this way one may have multiple channels for a given code length. However, in general, the LiDAR/radar/sonar must be pointed at targets with a hard surface (such as the surface of the earth) no farther than the distance to the first code to avoid range-wrapping issues. In addition, it may be advantageous to either subtract the average from the code or from the data prior to processing to help alleviate noise/bias issues.

Figure 9:
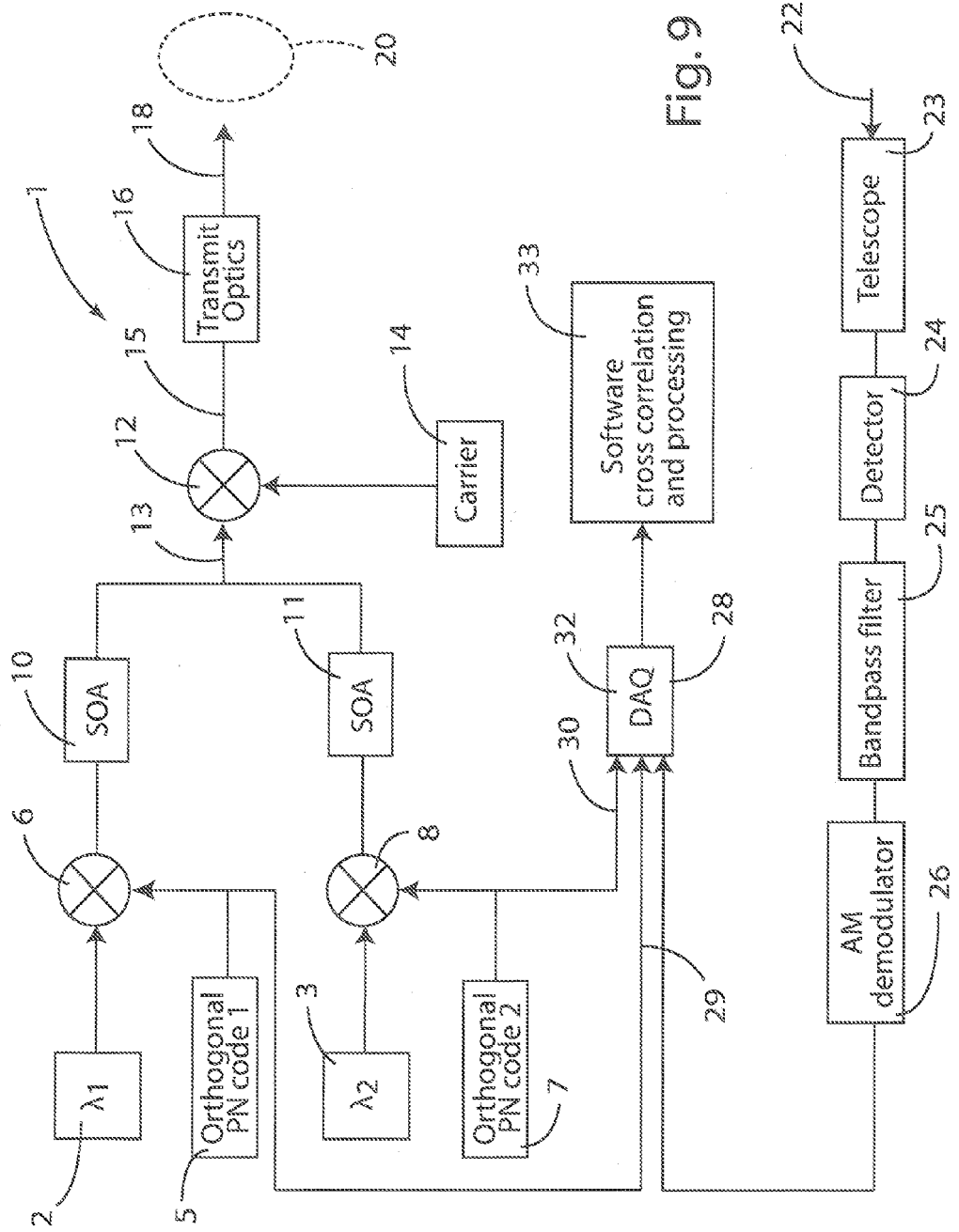
FIG. 9 is a block diagram of a CW LiDAR system with an AM modulated carrier.

With further reference to FIG. 9, a CW LiDAR system 1 according to one aspect of the present invention utilizes an AM modulated carrier. The CW LiDAR system 1 includes a first laser 2 and a second laser 3. Although various lasers having different wavelengths could be utilized, in the illustrated example the first and second lasers 2 and 3, respectively, may have a wavelength of about 1.57 microns. In general, the lasers 2 and 3 have slightly different wavelengths having different absorptions with respect to a particular gas or other substance. The first laser 2 may be selected to correspond to an absorption line of a particular chemical species. This depends on the chemical species to be measured. For example, there are numerous absorption lines at numerous different wavelengths. Thus, the wavelength of 1.57 microns is but one example of a suitable wavelength. In general, the second laser 3 has a different wavelength having a relatively small absorption coefficient with respect to the gas to be measured. Furthermore, one or more additional lasers (not shown) having wavelengths that are not equal to the wavelengths produced by the first and second lasers 2 and 3, respectively, may also be included in the CW LiDAR system 1. In general, the use of lasers having different wavelengths in differential absorption LiDAR is known, and the details with respect to selecting appropriate lasers for detecting a specific gas or other substance are not therefore described in detail herein.

A PN code generator 5 (see also FIG. 1) produces a first orthogonal PN code that is utilized to modulate the light from laser 2 as shown schematically at junction 6 of FIG. 9. Similarly, a PN code generator 7 modulates light from second laser 3 at junction 8. The PN code generators 5 and 7 may comprise a device or it may comprise software. It will be understood that FIG. 1 may represent a device, software, or it may be used as a mathematical representation for generating M1 sequences. Light from the junctions 6 and 8 is amplified by Semiconductor Optical Amplifiers (SOA's) 10 and 11, respectively, to amplify the signal. The optical signal 13 from SOA's 10 and 11 may be modulated to include a carrier signal as shown schematically in FIG. 9 by carrier 14 and junction 12. In the example of FIG. 9, an amplitude modulated carrier is utilized. However, the inclusion of a carrier may not be required for all applications, and it will therefore be understood that the AM and FM modulated carriers shown in FIGS. 9 and 10 respectively, are optional. Optical signal 15 is then supplied to transmit optical device 16, which produces an optical signal 18 that is directed towards a target. In FIG. 9, the target is shown schematically in dashed lines as a circle 20. However, it will be understood that the target may comprise clouds, gasses, the surface of a planet, or other features an interest.

Light reflected from target 20 returns in the form of a return signal 22 that is gathered by a telescope 23. The light is then converted into an electronic form by a detector 24, and the electronic signal is then processed by a band pass filter 25 and AM demodulator 26. It will be understood that the telescope 23, detector 24, band pass filter 25 and AM demodulator 26 are an example of an arrangement in accordance with an embodiment of the present invention. However, other devices and configurations may also be utilized. The demodulated signal 28, first PN code 29, and second PN code 30 are supplied to a Digital Acquisition System (DAQ) 32, and software 33 provides for software cross correlation and processing according to the method/processes discussed in more detail above. Signal bias may be removed by software 33 as discussed above.

Figure 10:
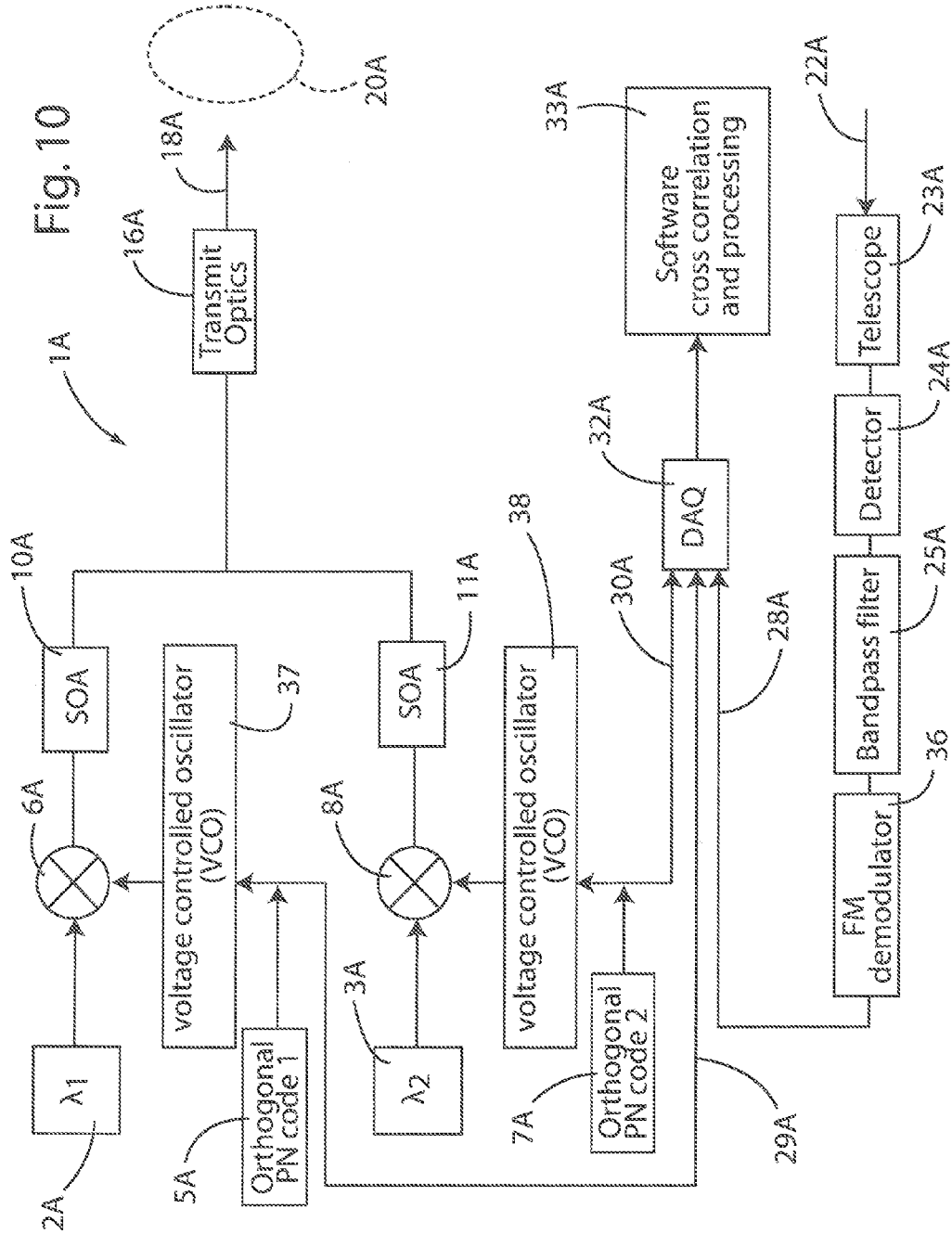
FIG. 10 is a block diagram of a CW LiDAR system with an FM modulated carrier.

With further reference to FIG. 10, an FM modulated CW LiDAR system 1A according to another aspect of the present invention includes many components that are substantially the same as the AM CW LiDAR system 1 of FIG. 9. The components of the FM CW LiDAR system 1A of FIG. 10 that are substantially similar to corresponding components of AM CW LiDAR system 1 of FIG. 9 are designated with the same part numbers, except that the suffix "A" has been added to the item numbers in FIG. 10. First and second orthogonal PN codes are provided by devices 5A and 7A. The orthogonal PN codes are provided to first and second Voltage Controlled Oscillators (VCO) 37 and 38, respectively, and light from first and second lasers 2A and 3A, respectively, is modulated at the junctions designated 6A and 11A. The combined optical signal 18A is directed towards a target 20A by transmit optics 16A. A return signal 22 is received by a telescope 23A, and is then converted into an electrical signal by detector 24A. The signal then passes through a band pass filter 25A and an FM demodulator 36. The first and second orthogonal PN codes are provided to a DAQ 32A by devices 5A and 7A, as is the demodulated electrical return signal 28A. Software 33A then provides cross correlation and processing as described in more detail above.

Figure 11:
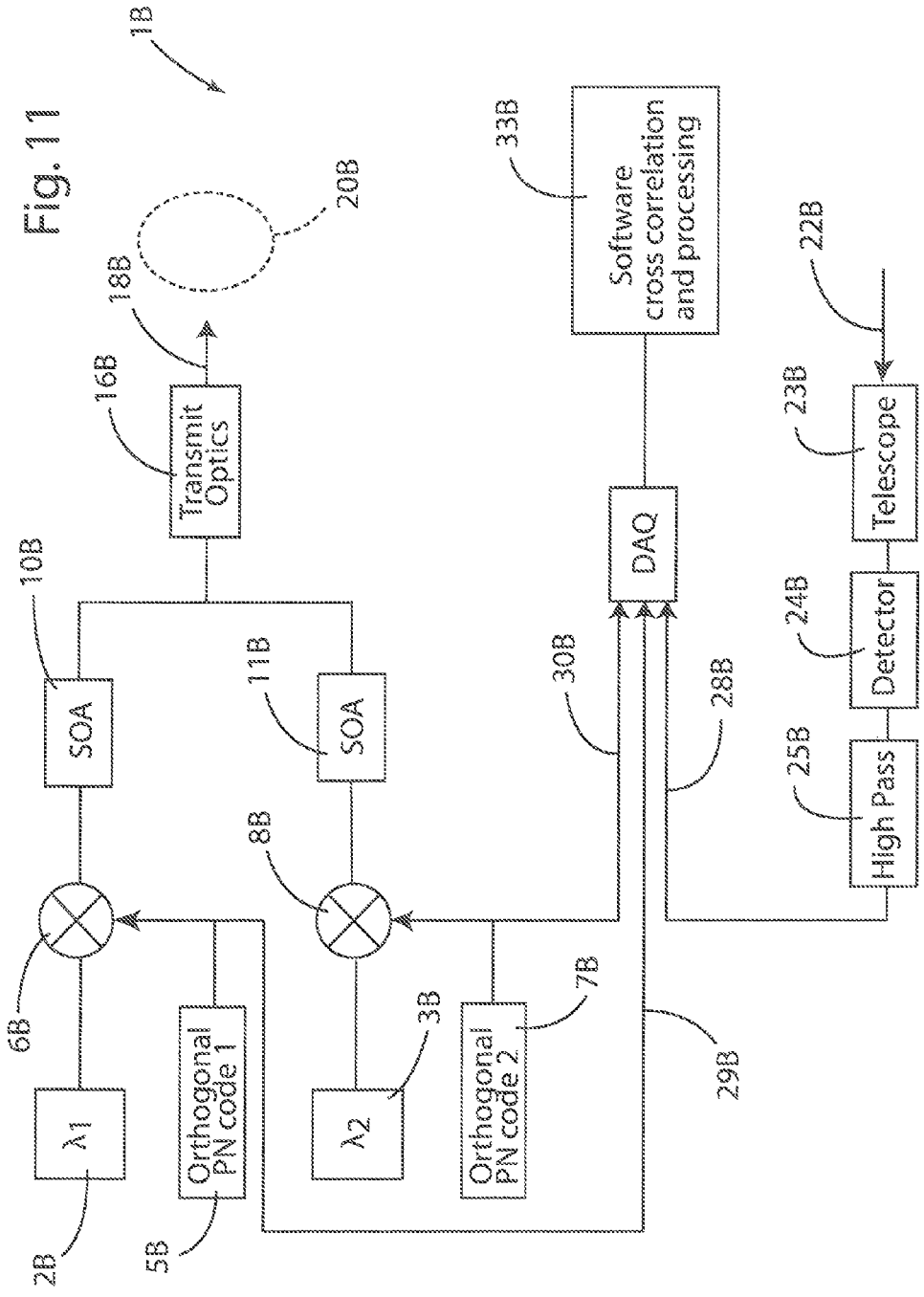
FIG. 11 is a block diagram of a CW LiDAR system that does not include a carrier.

With further reference to FIG. 11, a CW LiDAR system 1B according to another aspect of the present invention is somewhat similar to the AM CW LiDAR system 1 of FIG. 9 and the FM CW LiDAR system of FIG. 10. However, the CW LiDAR system 1B does not utilize a carrier signal. The CW LIDAR system of FIG. 11 includes first and second lasers 2B and 3B, and devices 5B and 7B that generate orthogonal PN codes. Alternatively, device 5B may generate unshifted PN code, and device 7B may generate PN code that is time shifted relative to the PN code generated by device 5B. The optical signal is amplified and transmitted towards a target 20B, and return signal 22B is received by a telescope 23B. A detector 24B and high pass filter 25B provide a signal 28B to DAQ 32B and software 33B for cross correlation and processing.

It will be understood that FIGS. 9-11 represent examples of ways to implement the present invention, but these examples are not intended to represent the sole ways to implement the invention. Various devices, software, and other such components may be utilized to implement the invention in LiDAR, radar and sonar systems.

Figure 12:
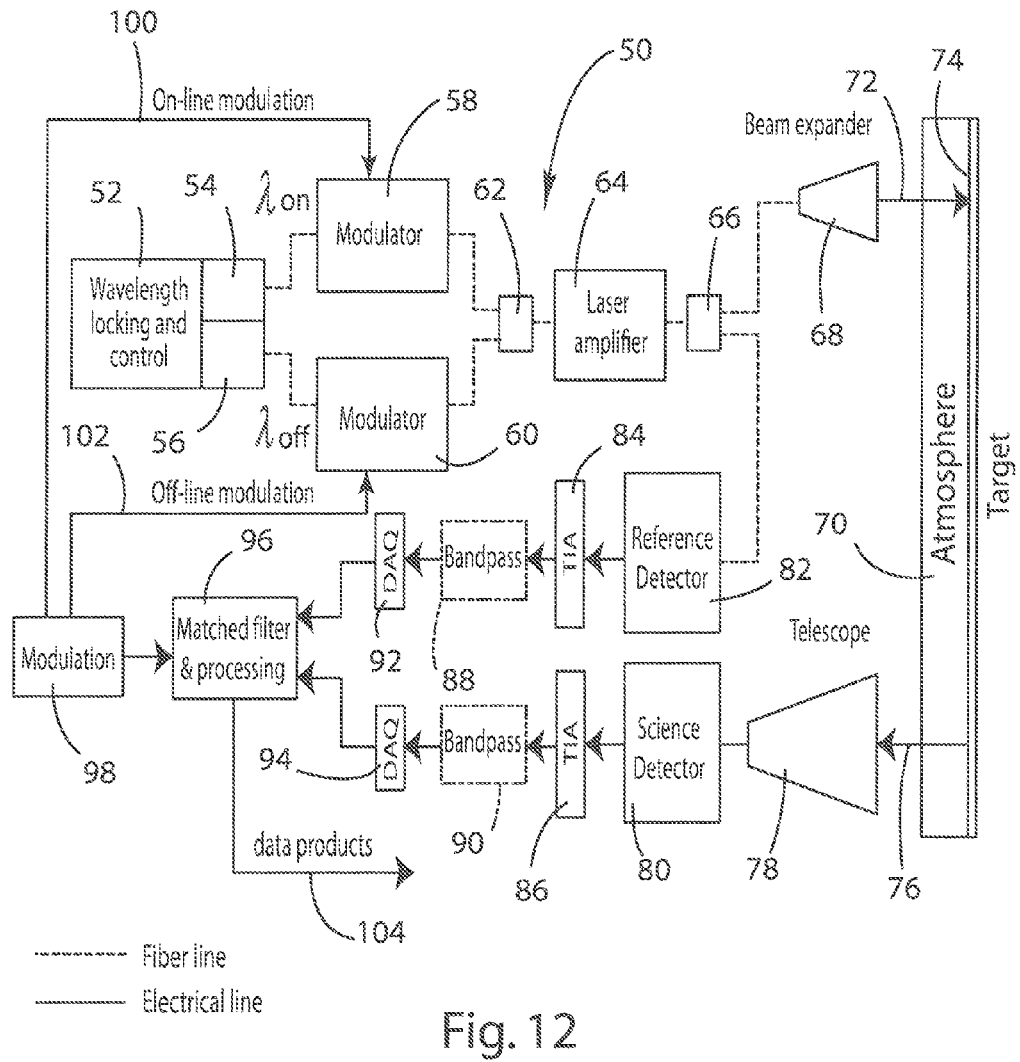
FIG. 12 is a baseline instrument block diagram of a LiDaR system according to another aspect of the present invention.

A IM-CW system 50 for CO2 IPDA measurements according to another aspect of the present invention is illustrated in FIG. 12. For this system, modulated online and offline lasers are combined at 62, then amplified at 64 and transmitted a beam expander 68 as a single laser beam 72 that is reflected back at 76. A very small portion of this transmitted signal is split off at 66 and routed to a reference detector 82 and digitized simultaneously with the data scattered back from ground 74 and other intermediate scatterers in the atmosphere 70 such as clouds and aerosols and received through a science detector 80 by means of a telescope 78. These reference and science data are further processed utilizing TIAs 84 and 86, respectively, optional band pass filters 88 and 90, respectively, and DAQs 92 and 94 respectively, to discriminate between ground and intermediate scatterers using the matched filter 96, and to obtain differential absorption power ratio and range estimates. The resulting data products 104 can be further processed, stores, and analyzed as required.

The on-line and off-line laser modulation signals using the time shifted approach can be expressed as:

$$\Lambda_{off}=1+m\sigma(t),$$

$$\Lambda_{on}=1+m\sigma(t-\tau) \quad (10.0)$$

where m is the modulation index with a value between 0 and 1, $\sigma(t)$ is the repeating modulation waveform where $-1 \leq \sigma(t) \leq 1$, and $\tau$ is the time shifting of online modulation waveform related to that of offline. In general, $\tau > 2r_{max}/c$ is chosen so as to avoid interference between the time shifted channel and intermediate scatterers, where $r_{max}$ is the maximum distance among potential scatterers including the Earth's surface and also called unambiguous range, while c is the light speed. With the modulation waveforms of Equation 10.0, the received lidar off-line and on-line optical powers from a single target at range r are given by $$P_{rec\_off}(t) = \quad (11.1)$$
$$\frac{K}{r^2} P_{off} \exp\left(-2\varepsilon \int_0^r \beta(r')dr'\right) \exp(-2\xi)(1+m\sigma(t-2r/c))$$

$$P_{rec\_on}(t) = \frac{K}{r^2} P_{on} \exp\left(-2\varepsilon \int_0^r \beta(r')dr'\right) \quad (11.2)$$
$$\exp(-2\xi)\exp(-2\xi')(1+m\sigma(t-2r/c-\tau))$$

where $\xi$ is the total one-way column optical depth for the off-line measurement that is decided by the gas absorption other than $CO_2$, and $\xi'$ is the one-way column optical depth due to the $CO_2$ absorption, $\beta$ is the backscatter coefficient, $\epsilon$ is the extinction to backscatter ratio, K is a constant, where $P_{on}$ an $P_{off}$ the transmitted on-line and off-line powers, respectively. When multiple targets including surface exist in the lidar path length, each target would generate similar received lidar signals like those in Equations 11.1 and 11.2. The signals from these multiple targets are combined at the detector and converted to an electronic signal S(t). For an AC coupled receiving subsystem, we have, $$S(t) = \sum_k [C_{1k}m\sigma(t-2r_k/c-\tau) + C_{2k}m\sigma(t-2r_k/c)] \quad (12.0)$$

where we sum over all k scatterers and where, $$C_{1K} = \frac{K'_k}{r^2} P_{on} \exp\left(-2\varepsilon \int_0^{r_k} \beta(r')dr'\right) \exp(-2\xi_k)\exp(-2\xi'_k) \quad (13.1)$$

$$C_{2k} = \frac{K'_k}{r^2} P_{off} \exp\left(-2\varepsilon \int_0^{r_k} \beta(r')dr'\right) \exp(-2\xi_k) \quad (13.2)$$

where K' is a constant. These $C_{1k}$ and $C_{2k}$ returns can be uniquely discriminated from other returns from different scatterers using the matched filter of the transmitted waveform. For a ground target solve for $\xi_g'$ gives:

$$\xi' = \frac{1}{2}\ln\left(\frac{C_{2g}P_{on}}{C_{1g}P_{off}}\right) \quad (14.0)$$

Where $C_{1g}$ and $C_{2g}$ are the ground returns. Once $C_{1g}$ and $C_{2g}$ are determined the column optical depth for $CO_2$ can be found. In general, this is done by cross correlating the reference waveform with the return signal S(t), i.e., by the matched filter as mentioned before. This results in multiple peaks for these scatterers. The ground return can be identified through range gating (or maximum range). By choosing the reference modulation waveforms with perfect autocorrelation properties (ML sequence for instance), channel separation is achieved though the time shifting approach since each channel correlates at a different apparent range without interference between channels or scatterers. That is, each scatterer results in two peaks in matched filter output: one for offline, and the other for online with the $\tau$ shifted time. The details of this approach are discussed elsewhere (see, e.g. Joel F. Campbell, Narasimha S. Prasad, Michael A. Flood "Pseudorandom noise code-based technique for thin-cloud discrimination with $CO_2$ and $O_2$ absorption measurements," Opt. Eng. 50(12), 126002 (Nov. 18, 2011), doi:10.1117/1.3658758).

Band Pass Filtered Modulation Waveform Generation and Demodulation

The following is an improved modulation approach for $CO_2$ IPDA measurements according to one aspect of the present invention. This method modulates a sine wave carrier by an ML-sequence as in Equations 15.1 and 15.2 (below). To effectively represent each bit of ML-sequence in transmitted waveforms, and allow flexibility in the unambiguous range for a particular code length and sample rate, the ML-sequence is oversampled by M, where M is an integer so that each code bit of the ML sequence is represented by M points. That bit is used to modulate a sine wave that has exactly P cycles per code bit. In order to satisfy the Nyquist rule we must have M>2P. Let pn be the original ML-sequence and PN be the oversampled ML-sequence such that PN(n)=pn(int((n−1)/M)+1), where int is the integer part.

Amplitude Modulation

In the case of amplitude modulation, the modulation waveform takes on one of two forms.

$$\sigma_a(n) = PN(n)\cos(2\pi(n-\frac{1}{2})P/M), \tag{15.1}$$

$$\sigma_b(n) = PN(n)\sin(2\pi(n-\frac{1}{2})P/M) \tag{15.2}$$

The ½ factor is introduced to make the autocorrelation function symmetric.

Figure 13:
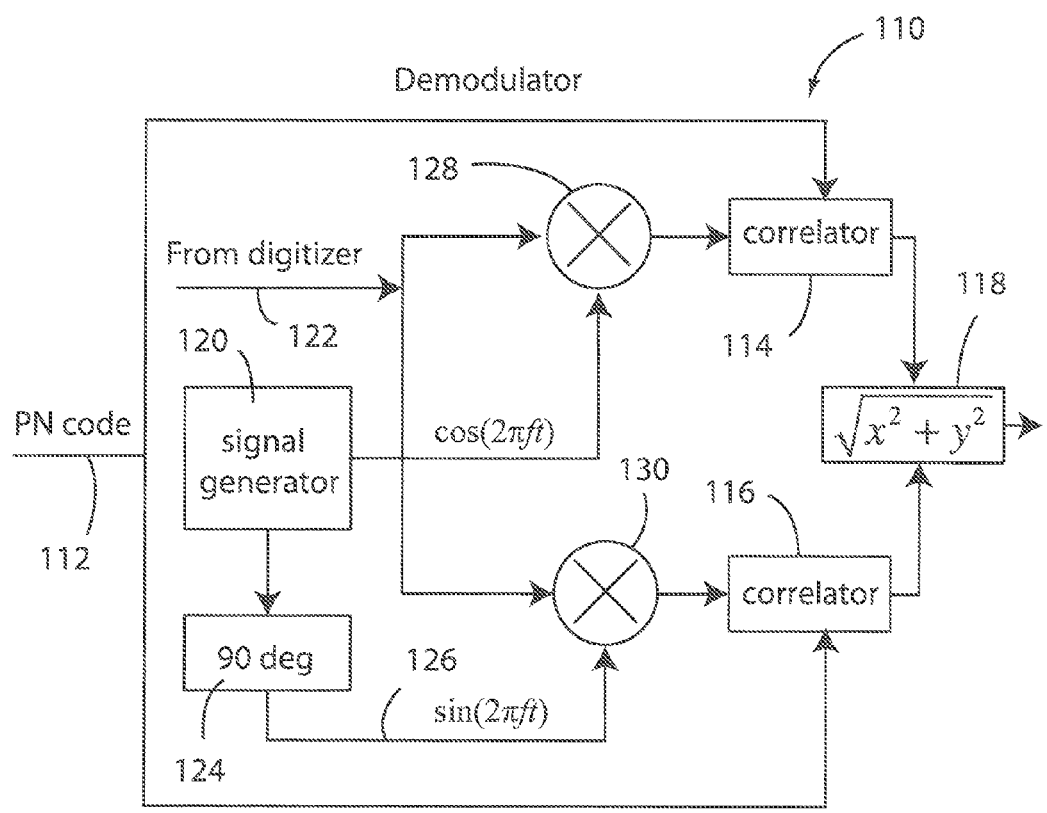
FIG. 13 is a block diagram of a quadrature matched filter correlator used for demodulation of the multichannel time shifted amplitude and phase modulated sine wave modulation signals, wherein the quadrature matched filter correlator is similar to a conventional quadrature demodulator except the low pass filter section has been replaced by a matched filter correlation with the reference PN code kernel.

Demodulation is accomplished as shown in FIG. 13 using the reference kernel of 2PN(n)−1. This for the reference kernel is necessary to get a resulting autocorrelation function with off pulse values of zero. This is a quadrature demodulator (see, e.g. Joel Campbell "Synthetic quadrature phase detector/demodulator for Fourier transform spectrometers," Applied Optics, Vol. 47, Issue 36, pp. 6889-6894 (2008)) with the low pass filter replaced by a matched filter correlation with the oversampled ML-sequence. The correlations may be efficiently computed with an FFT and take the form:

$$R(ref, \text{data}) = \tag{16.0}$$

$$\frac{1}{N} \sum_{m=0}^{N-1} ref^*(m) \, \text{data}\,(m+n) = DFT^{-1}(DFT^*(ref)DFT(\text{data})),$$

Where "*" denotes the complex conjugate, and N is the length of oversampled ML-sequence.

Figure 14A:
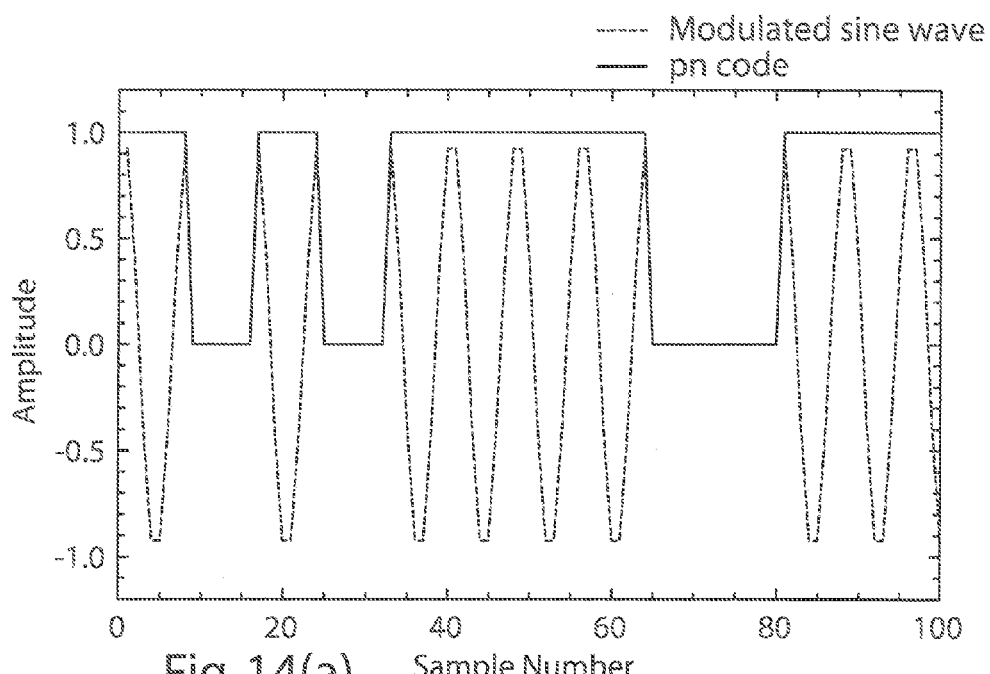
FIG. 14A is a plot of a cosine wave modulation for an amplitude modulation case according to equation 15.1.
Figure 14B:
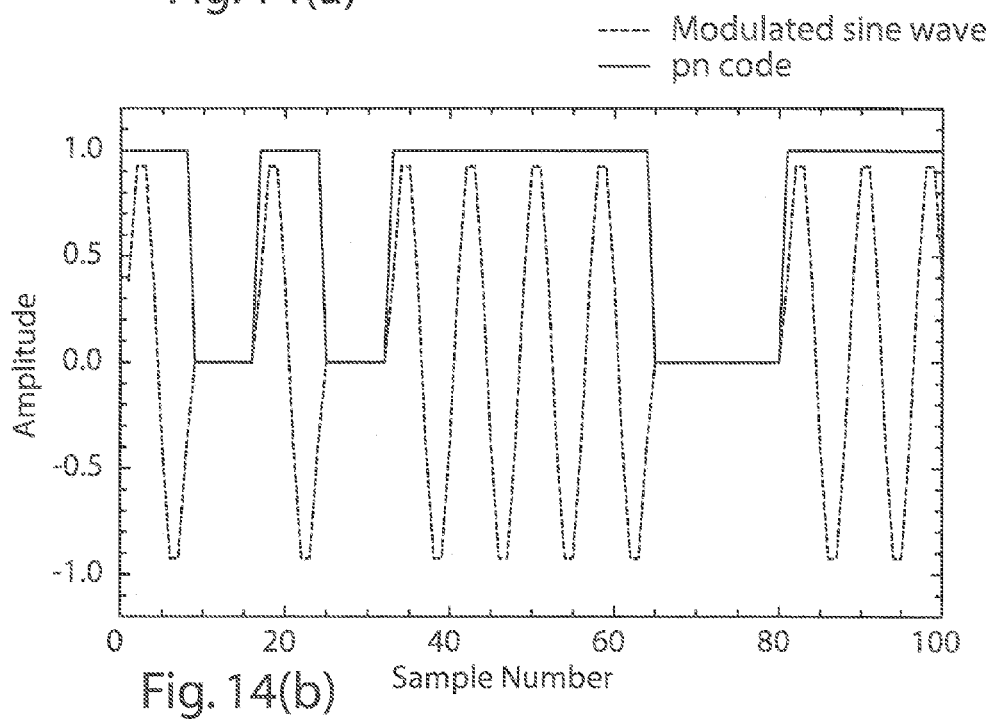
FIG. 14B is a plot of a sine wave modulation for an amplitude modulation case according to equation 15.2.

As an example of a modulation technique that is suitable for a band pass filtered LAS system as shown in FIG. 12, a special case is taken where P:=1 (one cycle per code bit) and M=8 (8 samples per code bit). An 8th order (or 255 length) ML-sequence is generated using the recurrence relation pn (n+8)=pn(n)⊕pn(n+2)⊕pn(n+5)⊕pn (n+6) with the seed {1, 0, 1, 0, 1, 1, 1, 1} for pn(1) through pn(8), where ⊕ is the "exclusive or". This is oversampled by a factor of 8. FIGS. 14(a) and 14(b) show a comparison between the cosine wave vs. sine wave modulation as in Equations 15.1 and 15.2 each modulation waveform produces a different autocorrelation function. Each waveform in FIGS. 14(a) and 14(b) as well as the additional Figs. discussed below were plotted at 8 samples per code bit with linear interpolation between points.

Figure 15A:
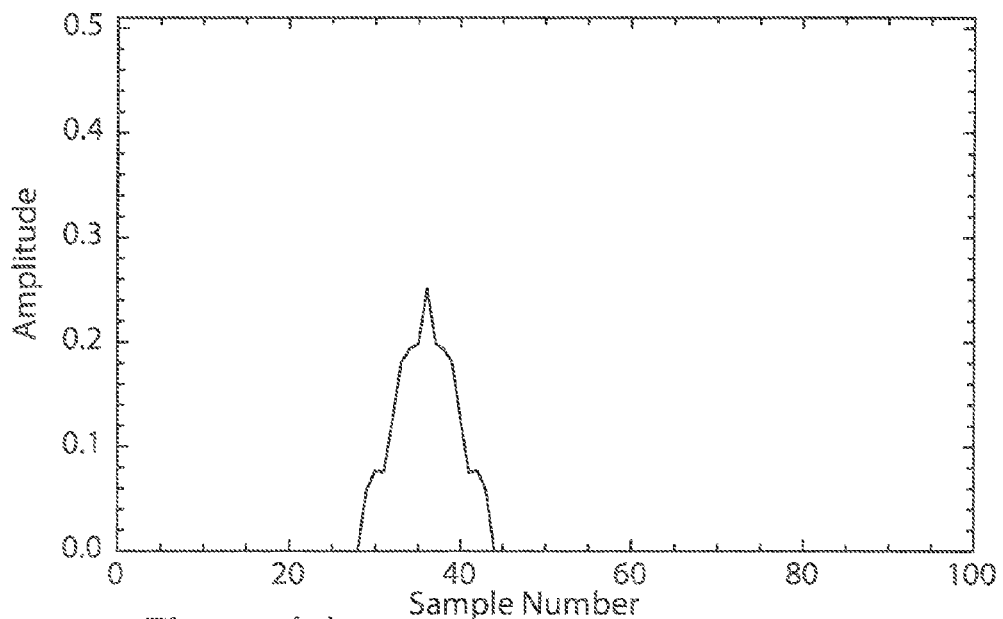
FIG. 15A is a plot of an autocorrelation function for a cosine wave with ML-sequence modulation with 1 cycle per code bit and 8 samples per code bit.
Figure 15B:
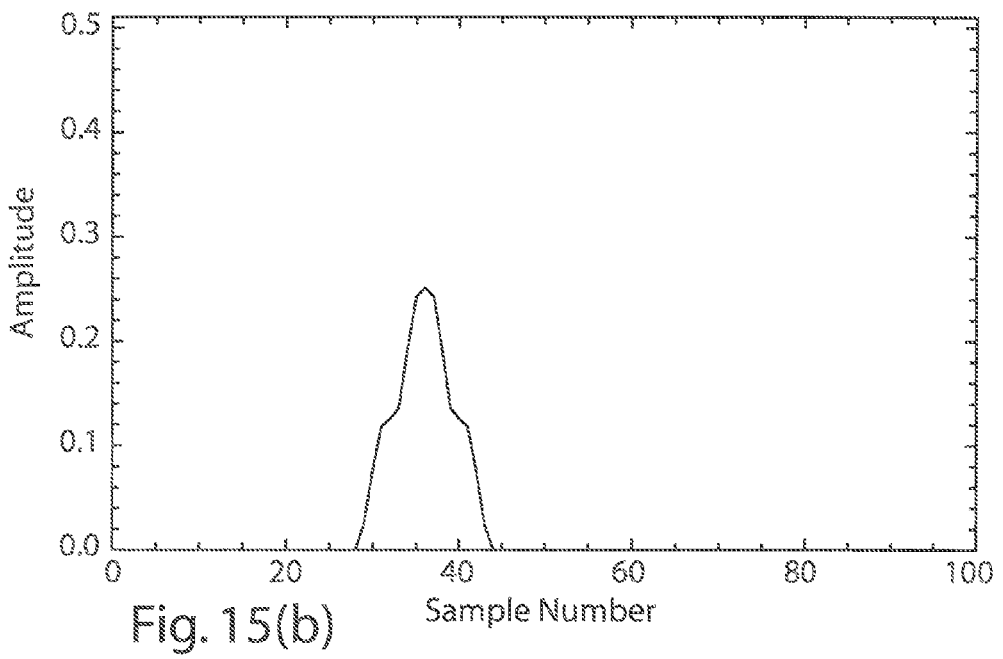
FIG. 15B is a plot of an autocorrelation function for a sine wave with ML-sequence modulation with 1 cycle per code bit and 8 samples per code bit.

The autocorrelation function may be computed according to the block diagram of FIG. 13. The results for both the cosine and sine wave cases are shown in FIGS. 15(a) and 15(b), respectively. The half height width is identical to the pure ML-sequence case.

It can be shown that the half height width for both the cosine and sine wave cases is identical to the pure ML-sequence case, though the sine wave case may be better suited for absorption measurements because of the more rounded peak. An autocorrelation function with a very sharp peak may have a height that is sensitive to under sampling. The sine wave case is less sharp than the pure ML-sequence. In both cases, and within the accuracy of numerical calculations, the off pulse values are approximately zero with the chosen parameters and normalization. The resolution of discriminating different targets is close to the pure ML-sequence case of c/2Br [4,5], where Br is the code bitrate (number of code bits per second), which is related to the effective modulation bandwidth.

PSK Modulation

A type of PSK modulation can be described in the following way. The modulation waveform considered here takes on one of two forms.

$$\sigma'_a(n) = (2PN(n)-1)\cos(2\pi(n-\frac{1}{2})P/M), \tag{17.1}$$

$$\sigma'_b(n) = (2PN(n)-1)\sin(2\pi(n-\frac{1}{2})P/M) \tag{17.2}$$

Figure 16A:
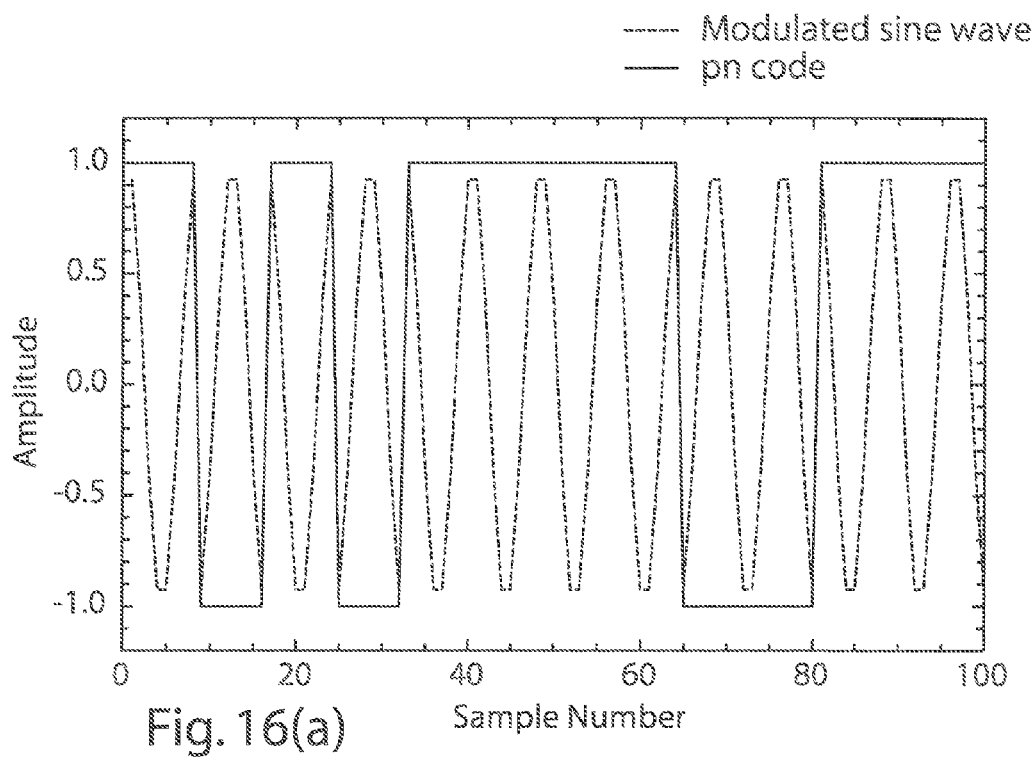
FIG. 16A is a plot of a cosine wave modulation for PSK modulation case as in equation 17.1.
Figure 16B:
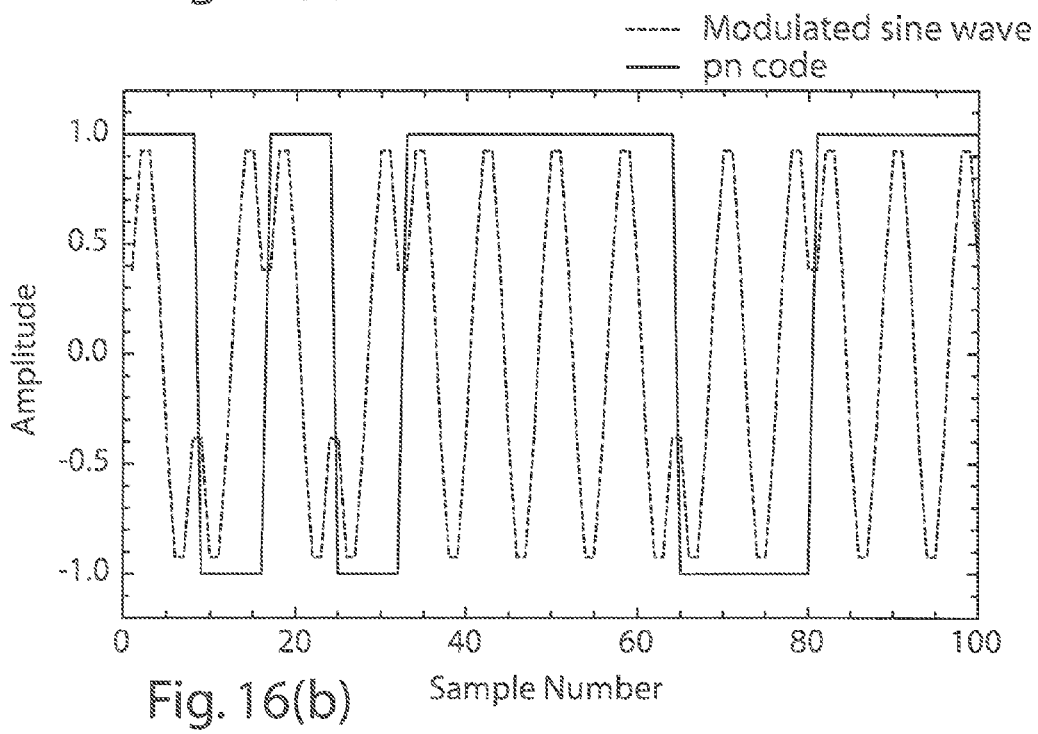
FIG. 16B is a plot of a sine wave modulation for PSK modulation case as in equation 17.2.

As in the previous case, the ½ factor is introduced to make the autocorrelation function symmetric. This is very similar to the amplitude modulation case except PN(n) has been replaced by 2PN(n)−1. FIGS. 16(a) and 16(b) provide a comparison between the cosine wave vs. sine wave modulation as in Equations 17.1 and 17.2, respectively.

Demodulation is accomplished using the quadrature correlator shown in FIG. 13. This demodulation is significantly different than some conventional PSK demodulation techniques and is particularly useful in the time shifted channels approach as it allows one to separate channels without the need to decode the phase directly, thus allowing the use of multiple PSK modulated laser signals that share the same modulation bandwidth. According to one aspect of the present invention, the reference kernel PN(n) may be used. This reference kernel provides a resulting autocorrelation function with off pulse values of zero in the case of PSK. The autocorrelation function is identical to that shown in FIGS. 15(a) and 15(b) in the case where P=1 (one cycle per code bit) and M=8 (8 samples per code bit). In spite of identical autocorrelation functions, this case has a major advantage. Since PN(n) is used as a kernel as opposed to 2PN(n)−1, this method has better noise immunity. The reason is because PN(n) is 0 for half of the length, which means we correlate over half the noise compared to the amplitude modulated case. As a result, the predicted SNR is improved by a factor of 2.

Hybrid Pulse/CW Modulation

Figure 17:
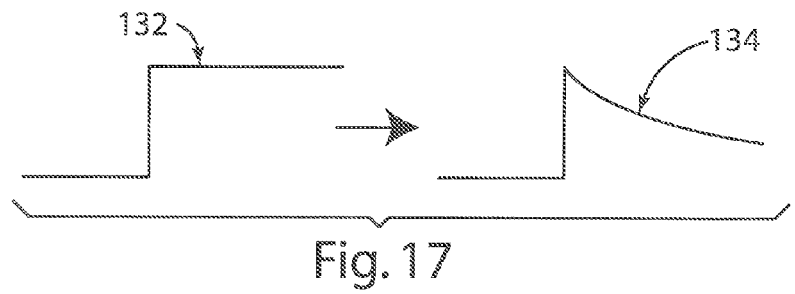
FIG. 17 is a plot of the step response (signal modulation) of an Erbium-Doped Fiber Amplifier (EDFA)

An alternative implementation utilized electronics that are DC coupled. This may be achieved by deleting the band pass filters of FIG. 12. In this case, the laser amplifier comprises an erbium-doped fiber amplifier (EDFA). There are at least two types of modulation possible with an EDFA amplifier. The first is pump modulation. With pump modulation there is a low pass filter response (see e.g. J. Freeman and J. Conradi "Gain modulation response of erbium-doped fiber amplifiers," Photonics Technology Letters, IEEE, Vol. 5, Issue 2, pp. 224-226 (1993)). This would be an ideal configuration but it requires an optical amplifier for each channel. However, with signal modulation as has been used in the past (see e.g., Jeremy T. Dobler, F. Wallace Harrison, Edward V. Browell, Bing Lin, Doug McGregor, Susan Kooi, Yonghoon Choi, and Syed Ismail "Atmospheric CO2 column measurements with an airborne intensity-modulated continuous wave 1.57 μm fiber laser lidar," Applied Optics, Vol. 52, Issue 12, pp. 2874-2892 (2013)), which allows one to use the same amplifier for all channels, this system behaves as a lead compensator circuit (J. Freeman and J. Conradi "Gain modulation response of erbium-doped fiber amplifiers," Photonics Technology Letters, IEEE, Vol. 5, Issue 2, pp. 224-226 (1993)), which is similar to a high pass filter. The step response 134 of such an amplifier configured for signal modulation, which is shown in FIG. 17, does not fully follow the input step function 132. This is due to an excited state population depletion, which then settles to a steady state.

Even if there is electronic DC coupling in the transmitter and receiver electronics, the nature of the optical amplifier used in this example to degrade the autocorrelation properties due to the distortion of the PN code. In order to maintain the integrity of the input signal the laser is continually pumped at the signal level to avoid this effect. One solution is to build this pumping into the modulation signal. Different types of sine wave modulation discussed before can fulfill this purpose. An alternative is to turn the PN code on and off at a regular rate. This can be done with a square wave if enough bandwidth is available. A simple method is to modify Equations 15.1 (and 15.2) to:

$$\sigma(n) = (1 - \cos(2\pi(n-1/2)P/M))PN(n) - 1 = \qquad (18.0)$$
$$2\sin^2(\pi(n-1/2)P/M)PN(n) - 1$$

Figure 18:
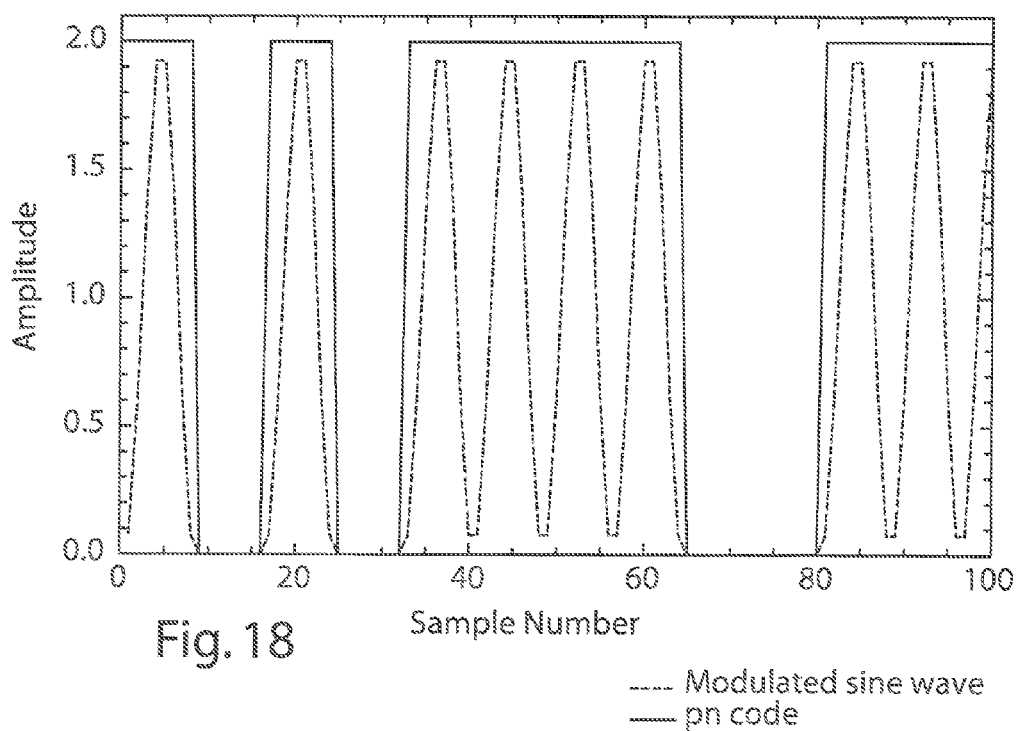
FIG. 18 is a plot of a hybrid sine wave pulse laser modulation signal, γ, using the modulation wave form of equations 17.1 and 17.2, assuming m=1.

An example of this modification is shown in FIG. 18 with the first 100 points of the modulation waveform. For this example, P=1 and M=8 are selected. This modification has at least one significant advantage over the previous technique: for the same amplitude it uses only half the average optical power. The reason is because in order to transmit the previously described modulation it must be offset. This means that a logical zero in that case is half the peak laser power whereas in this case a logical zero is zero power.

Figure 19:
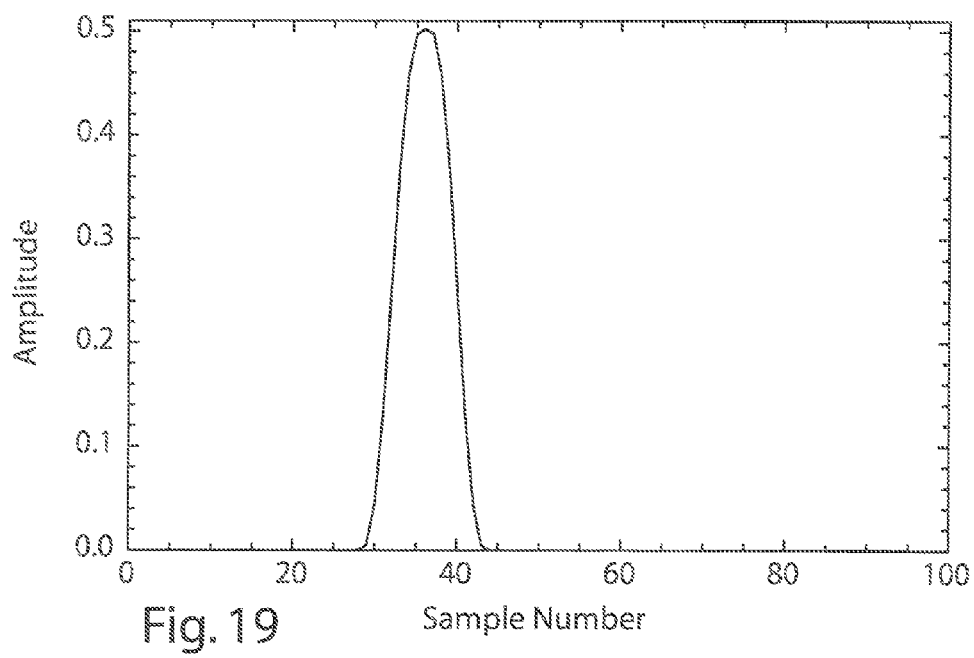
FIG. 19 is a plot showing an autocorrelation function for hybrid pulse modulation.

Demodulation of this signal is relatively straight forward. Instead of demodulating the result using the block diagram in FIG. 13, the return signal is correlated with 2PN−1. The resulting autocorrelation function is shown in FIG. 19.

As in the previous case, the half height width is identical to the pure ML-sequence modulation. However, due to the more rounded peak of the autocorrelation function, the height measurement, which is necessary for accurate CO2 absorption measurements, should be less sensitive to sampling than with the sharp peak of the pure ML-sequence case or the ML-sequence modulated sine wave case in the previous section. Yet the autocorrelation properties are near perfect as those in previous cases with the chosen parameters and normalization.

In many LAS implementations it is desirable to limit the bandwidth of the PN code to reduce aliasing and thereby minimize sampling error in the measurement of the amplitude height of the autocorrelation function. This is provides accurate absorption measurements and makes the peak height less sensitive to small changes in range. However, known filters may not accomplish this requirement. For example, some known filters such as square window filter or other high order filter, may introduce sidelobes to the autocorrelation function. Gaussian filters are sometimes used in digital communications to bandwidth limit digital data, Minimize channel bleed-over, and carry the maximum amount of information with the least bandwidth (see e.g. Conditions J. Math. Phys. 35, 1471 (1994)). A convenient implementation is to use a periodic version of a Gaussian filter so that the filter can be terminated at the end of a cycle. Since a DFT contains the frequency content in the first half of the array, and a mirror image in the second half, and the PN code itself is transmitted as a repeating waveform, a cyclic filter convolution is appropriate.

A periodic Gaussian can be constructed in the following way with:

$$G(x) = \sum_{n=-\infty}^{\infty} \exp((x-nL)^2/2\sigma^2) \qquad (19.0)$$

Here L is the period and $\sigma$ is the standard deviation. This sum can be done analytically as:

$$\sum_{n=-\infty}^{\infty} \exp((x-nL)^2/2\sigma^2) = \qquad (20.0)$$
$$\sqrt{2\pi}\left|\frac{\sigma}{L}\right|\left[1 + 2\sum_{n=0}^{\infty} q^{n^2}\cos(2\pi nx/L)\right] \equiv \sqrt{2\pi}\left|\frac{\sigma}{L}\right|\vartheta_3(\pi x/L, q)$$

where $\theta_3$ is the Jacobi theta function of the third kind and the nome q is given by:

$$q = \exp(-2\pi^2\sigma^2/L^2). \qquad (21.0)$$

Theta functions are widely used in the theory of elliptic functions (see e.g., John J. Benedetto, Georg Zimmermann "Sampling multipliers and the Poisson summation formula," J. Fourier Anal. Appl., Vol. 3, Issue 5, pp 505-523 (1997)) and other applications (see e.g. Joel Campbell "The SMM model as a boundary value problem using the discrete diffusion equation," Theor. Popul. Biol., Vol. 72, Issue 4, pp. 539-546 (2007) and Joel Campbell "Ground state energy for the Hartree-Fock equations with Dirichlet boundary"). In order to scale this so that is 1 at the maxima we have:

$$W(x,L,q) = \theta_3(\pi x/L,q)/\theta_3(0,q) \qquad (22.0)$$

To apply this as a filter in the frequency domain we simply multiply the DFT by the array W(n−1, N, q) and the inverse DFT is taken, where N is the length of the array and 1≤n≤N. To show the usefulness of this filter we first show how to limit the bandwidth of an MLsequence and show how the autocorrelation properties and resolution are preserved. That bandwidth limited sequence is then used in the modulation examples discussed in the previous sections to show both the effect of bandwidth limiting and preservation of the near perfect autocorrelation properties for each case with only a minor degradation in resolution.

Theta Function Filtered ML-Sequence

Figure 20:
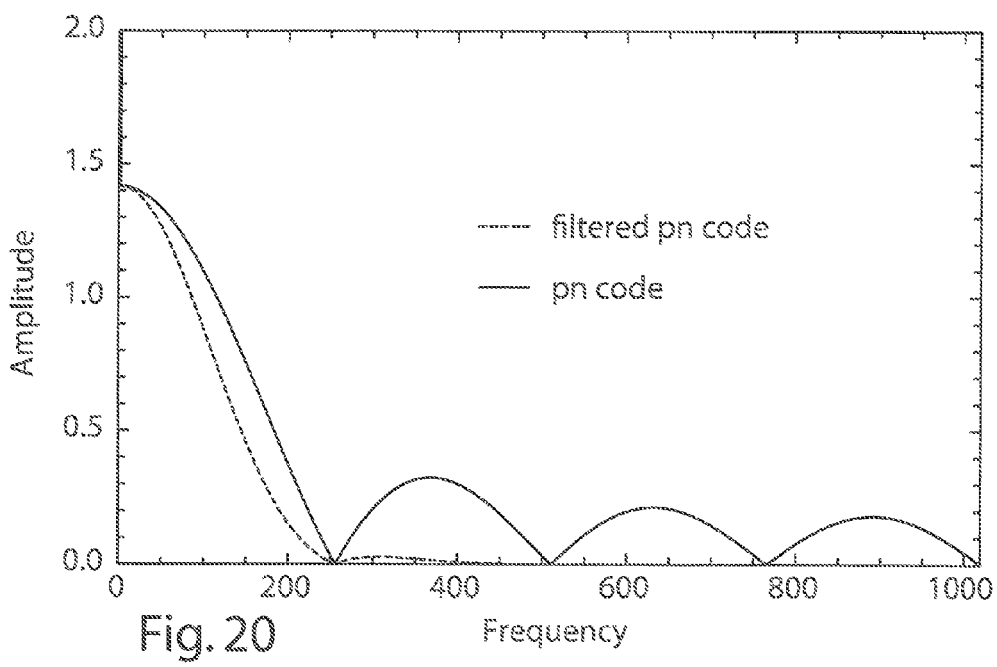
FIG. 20 is a plot showing a comparison of frequency content of filtered vs. unfiltered PN code.

First, take the simple case of a pure ML sequence with length 255 and oversampled by a factor of 8 as in the previous section. This is filtered with the theta function filter with q=0.9 and N=255×8=2040. A plot of the unfiltered vs. filtered PN code frequency content is shown in FIG. 20. Filtered pn code bandwidth is well under the Nyquist sampling rate demonstrating aliasing is no longer an issue.

Figure 21:
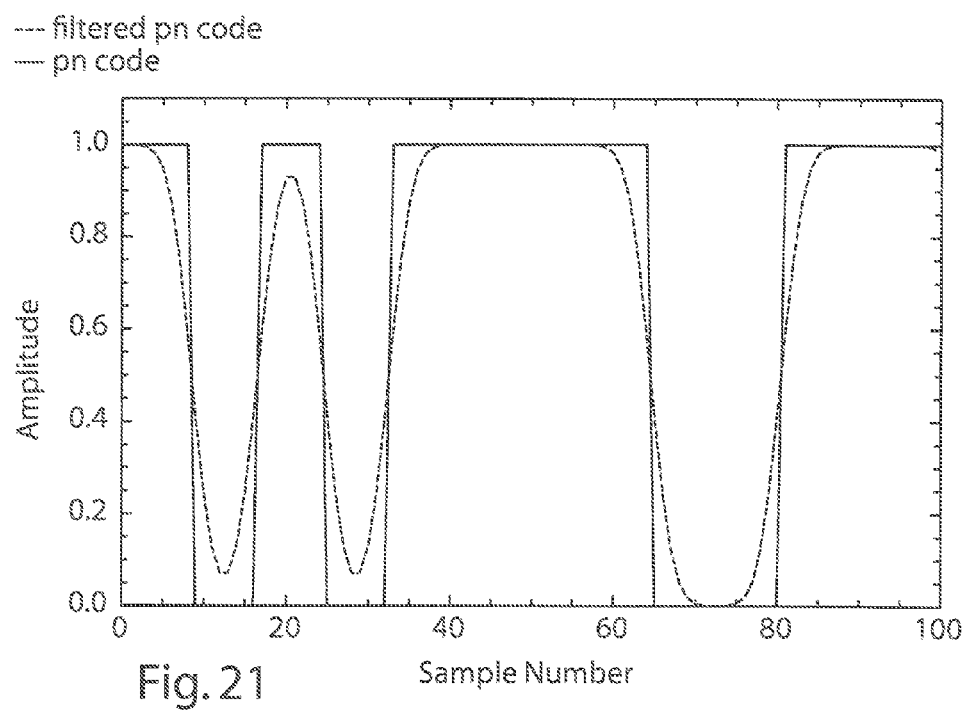
FIG. 21 is a plot showing a comparison between filtered PN code and unfiltered PN code.

A plot of unfiltered vs. filter PN code is shown in FIG. 21. This is the result of a circular convolution between the cyclic theta function filter and the cyclic PN code.

Figure 22:
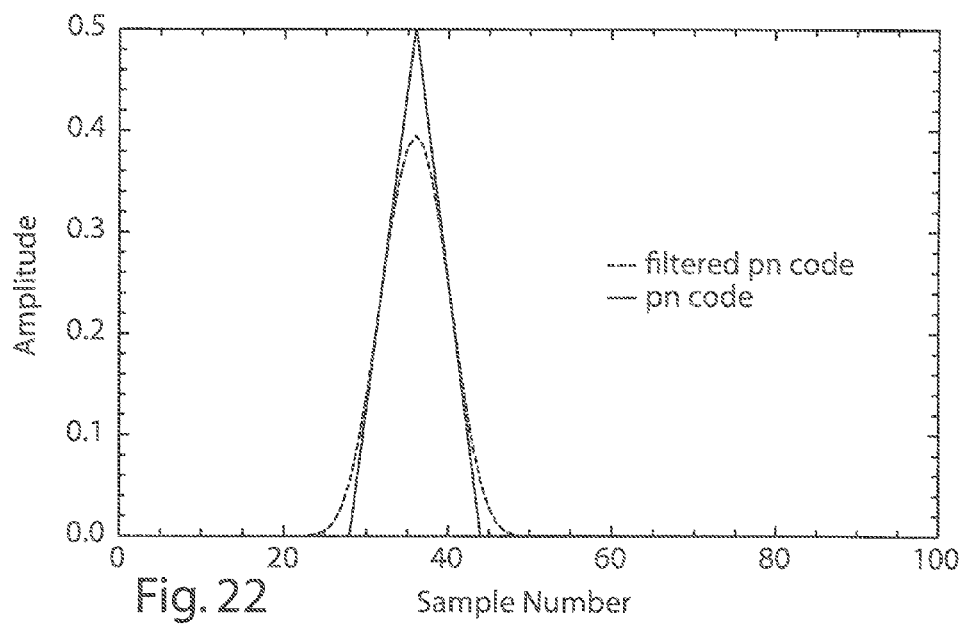
FIG. 22 is a plot showing an autocorrelation function for filtered vs. unfiltered PN code wherein the filtered case was correlated with an unfiltered reference.

FIG. 22 is the result of the correlation between 2PN−1 and both the filtered and unfiltered PN code. In spite of the strong filtering, the pulse width is very similar, and the peak is more rounded, which is a desirable trait. The off pulse values are zero to within numerical precision.

Amplitude Modulations Case Using Theta Function Filtered PN Code

Figure 23:
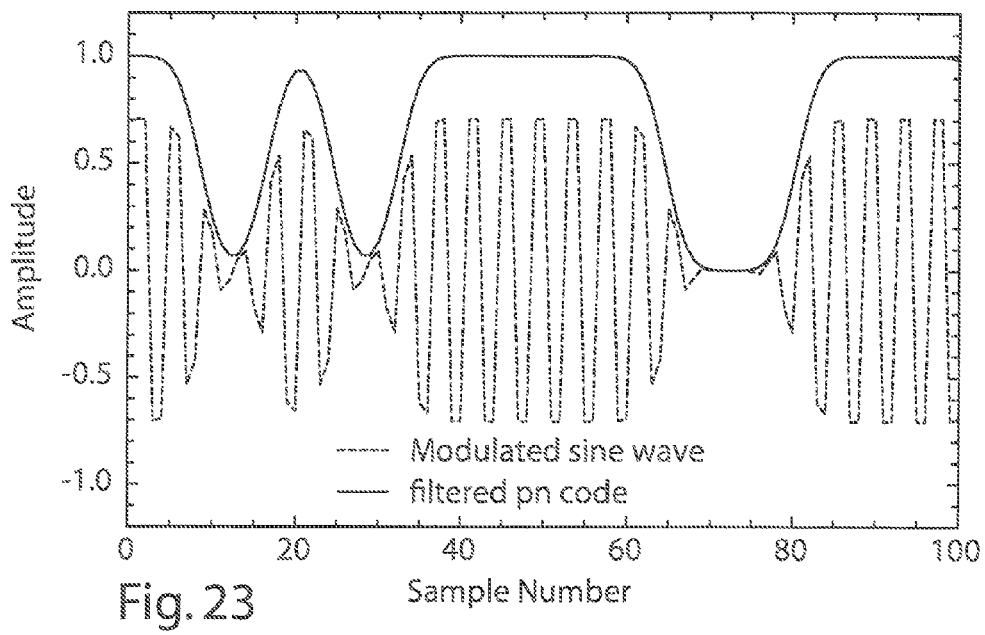
FIG. 23 is a plot showing filtered PN code and resulting amplitude modulated sine wave.

This case uses the filter PN code described earlier to modulate a sine wave carrier as in $\sigma_b$ of Equations 15.1 and 15.2 with P=2 (2 cycles per code bit) and M=8 (8 samples per code bit). A plot of the resulting modulation is shown in FIG. 23.

Figure 24:
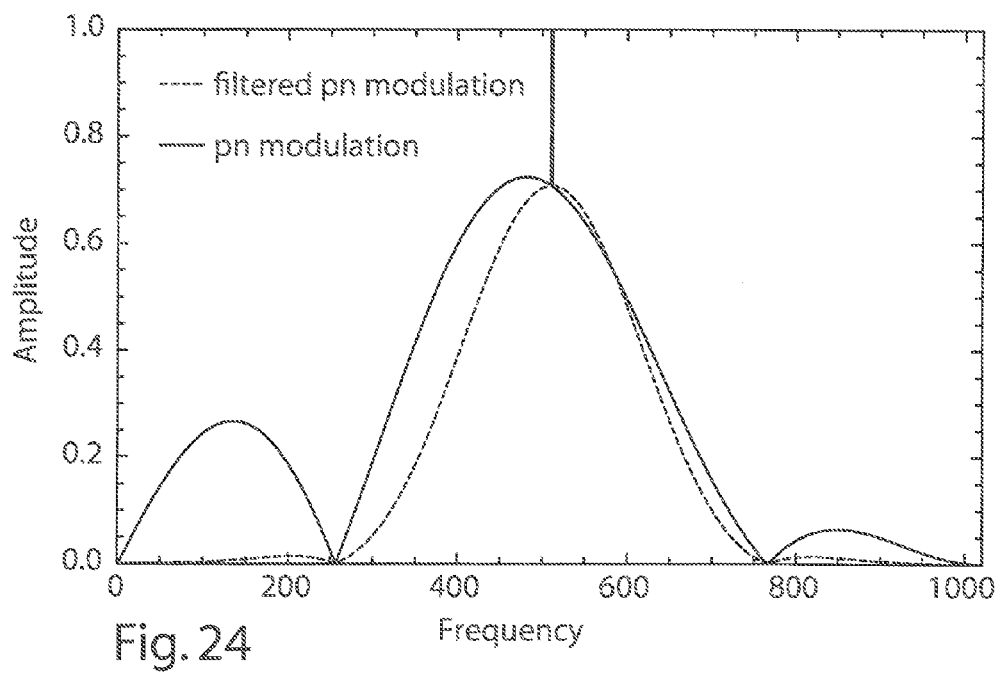
FIG. 24 is a plot showing frequency spectra of filtered modulation vs. unfiltered modulation.

FIG. 24 is a lot of the frequency spectra of the modulated sine wave. This shows the resulting frequency content of the filtered modulation is bounded within the Nyquist range with no aliasing.

Figure 25:
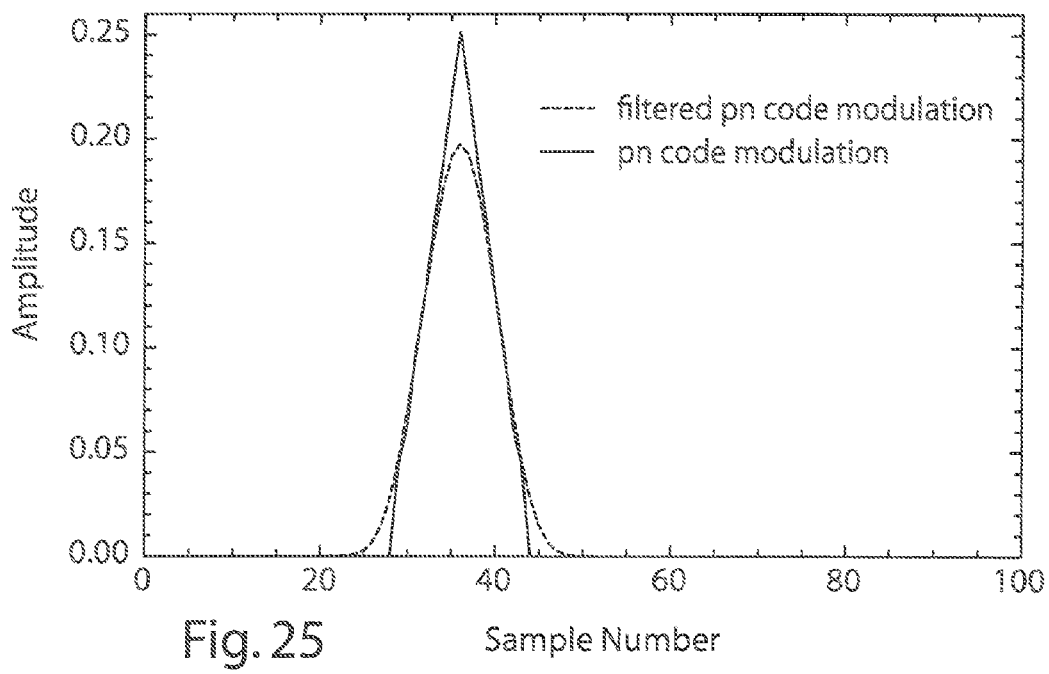
FIG. 25 is a plot showing a comparison of autocorrelation functions between a filtered modulation case and an unfiltered modulation case.

FIG. 25 is a plot of the autocorrelation function of the filtered vs. unfiltered pn modulation. This shows the modulation produces more robust matched filter output for peak determination by producing a more rounded peak, which is desirable for amplitude measurements in differential absorption estimation because it produces less sampling error. The resolution degradation is very minor, and off pulse values are zero to within numerical precision.

PSK Modulation Case Using Theta Function Filtered PN Code

Figure 26:
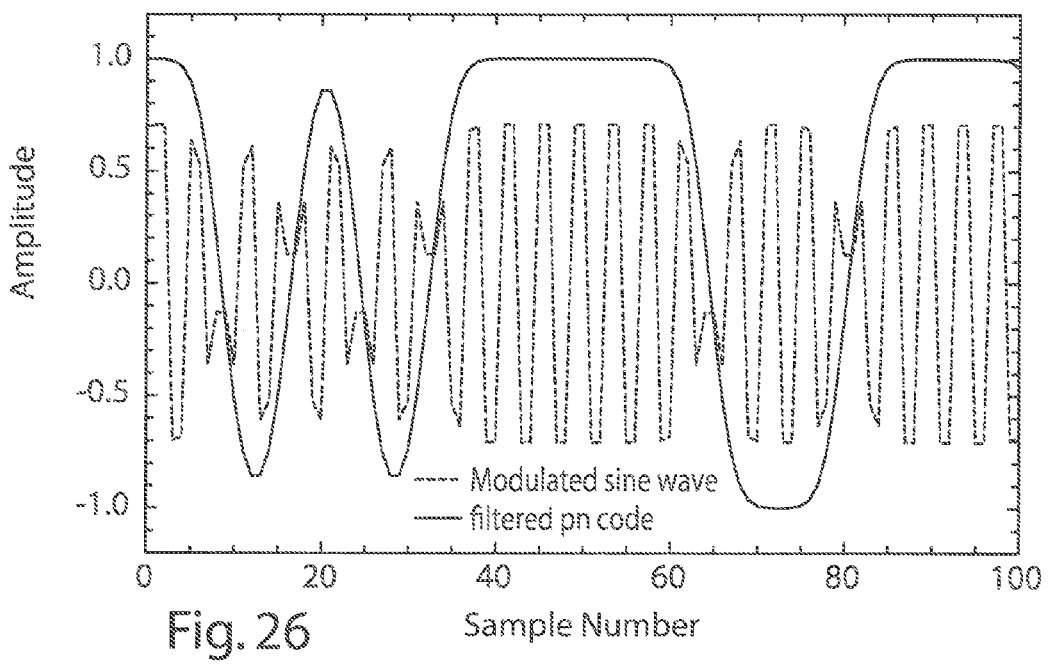
FIG. 26 is a plot showing filtered PN code and a resulting PSK modulated sine wave.
Figure 27:
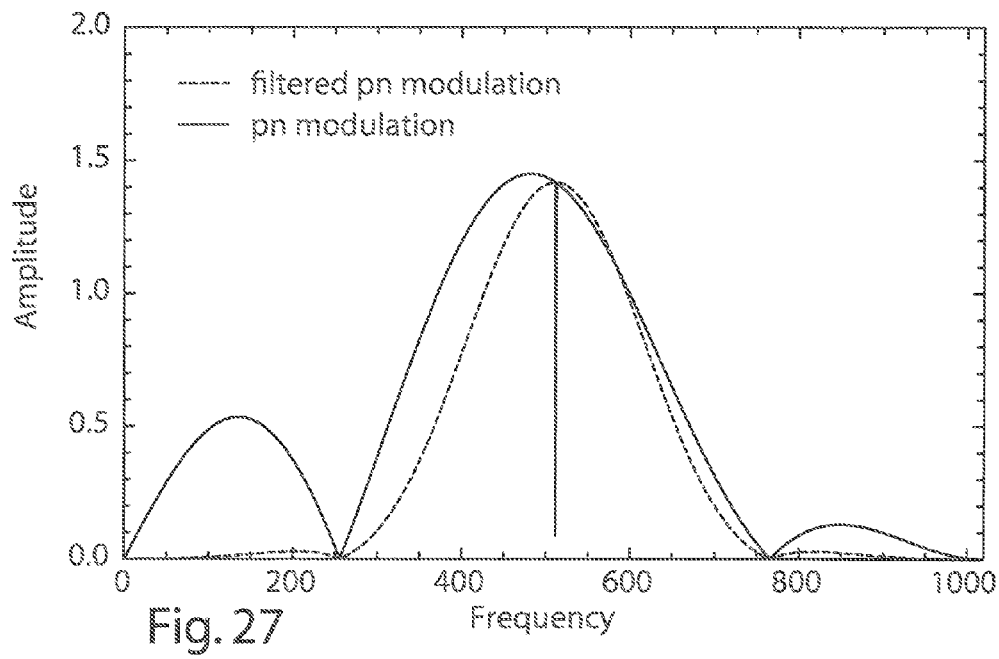
FIG. 27 is a plot showing frequency spectra of filtered modulation vs. unfiltered modulation.

This case uses the filtered PN code described earlier to modulate a sine wave carrier as in $\sigma'_b$ of Equation 18.0 with P=2 (2 cycles per code bit) and M=8 (8 samples per code bit). A plot of the resulting modulation is shown in FIG. 26.

The plot of the autocorrelation function of the filtered vs unfiltered pn PSK modulation is identical to FIG. 25 of the previous section.

Hybrid Pulse Modulation with Theta Function Filtered ML Sequence

Figure 28:
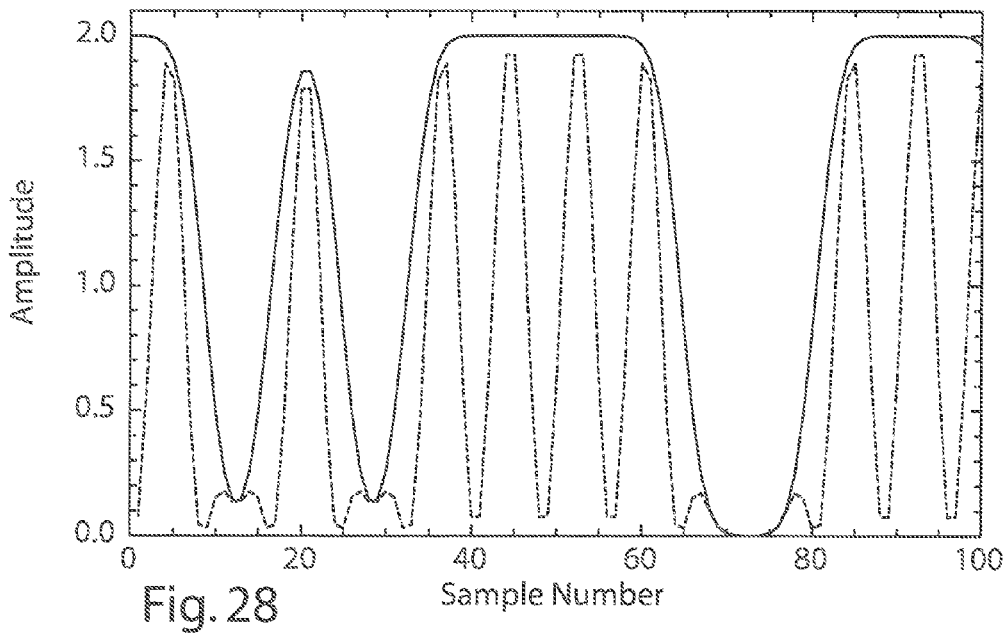
FIG. 28 is a plot showing hybrid pulse modulation with filtered PN code modulation.

We take the case using Equations 17.1 and 17.2 with P=1 (one cycle per code bit) and M=8 (8 samples per code bit), and use the same filtered PN code as in the previous two examples with q=9.0 FIG. 28 shows the resulting modulation.

Figure 29:
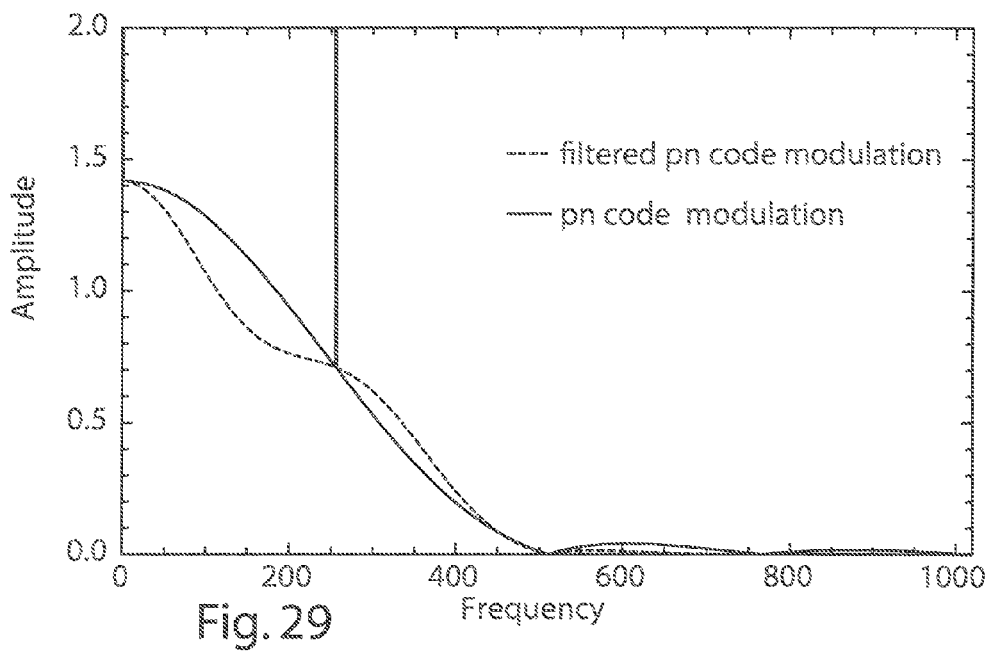
FIG. 29 is a plot showing a comparison of the frequency spectra between filtered and unfiltered hybrid pulse case.

The Resulting frequency spectra are shown in FIG. 29. The original modulation with the chosen parameters already does a good job at limiting the high frequencies as one might deduce from FIG. 17. This is because there are no sharp transitions as there are with the pure ML-sequence. The filtered version limits the spectra even more. Nyquest rate, but the unfiltered modulation has a limited bandwidth.

Figure 30:
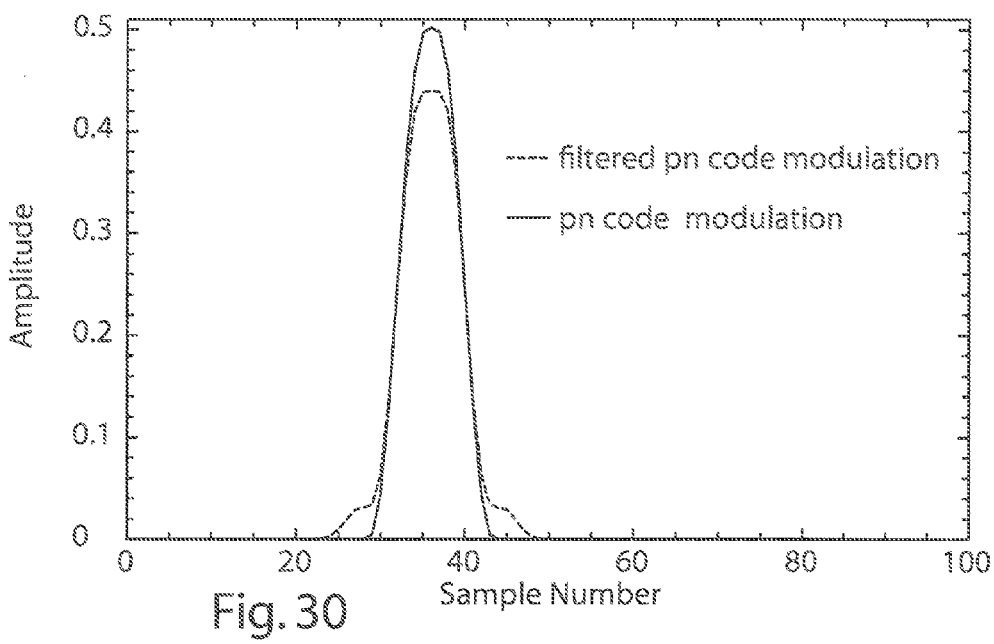
FIG. 30 is a plot showing a comparison between filtered vs. unfiltered autocorrelation functions.

FIG. 30 is a plot of the autocorrelation function of the filtered vs unfiltered pn code modulation. Both cases show very good autocorrelation properties, and off pulse values are zero to within numerical precision.

The three different PN modulation techniques described above can be used with different types of hardware. These include the baseline system (FIG. 12) with a signal modulated EDFA, the baseline system (FIG. 12) with the bandpass filters deleted, or the baseline system (FIG. 12) with the bandpass filters deleted and using separate EDFAs with pump modulation. In the case of DC coupled electronics combined with a laser amplifier with pump modulation, a pure ML sequence is ideal. In the case of the baseline, although the amplitude modulated sine wave version works well, the PSK modulation case discussed above may be superior in that it has superior signal to noise. If the electronics is DC coupled but the laser has a transient response such as the case with a signal modulated EDFA, the hybrid pulse version appears to be best.

The new cyclic filter based on the Jacobi theta function discussed above is useful for bandwidth limiting digital pn codes without seriously degrading the resolution and resulting in autocorrelation properties completely without sidelobes or other artifacts. A primary benefit is the reduction of aliasing, which reduces sampling error when measuring the amplitude of the autocorrelation function.

Appendix A: Periodic Gaussian as a Jacobi Theta Function

The sum represented by Equation 19.0 may be performed analytically using the Poisson summation formula "(see e.g. John J. Benedetto, Georg Zimmermann Sampling multipliers and the Poisson summation formula J. Fourier Anal. Appl., Vol. 3, Issue 5, pp 505-523 (1997))", which states:

$$\sum_{n=-\infty}^{\infty} f(n) = \sum_{k=-\infty}^{\infty} \hat{f}(k) \tag{A1}$$

where $$\hat{f}(k) = \int_{-\infty}^{\infty} f(n) \exp(-2\pi i k n) \, dn \tag{A2}$$

is the Fourier Transform of f. In the case of Equation 10.0 this becomes:

$$\hat{f}(k) = \int_{-\infty}^{\infty} \exp((x-nL)^2/2\sigma^2)\exp(-2\pi i k n) \, dn = \tag{A3}$$
$$\sqrt{2\pi} \left|\frac{\sigma}{L}\right| \exp(-2\pi^2\sigma^2 k^2/L^2)\exp(-2\pi k x/L)$$

so that $$F(x) = \sqrt{2\pi}\left|\frac{\sigma}{L}\right| \sum_{k=-\infty}^{\infty} \exp(-2\pi^2\sigma^2 k^2/L^2)\exp(-2\pi k x/L) = \tag{A4}$$
$$\sqrt{2\pi}\left|\frac{\sigma}{L}\right|\left[1 + 2\sum_{k=0}^{\infty} q^{k^2} \cos(2\pi k x/L)\right] = \sqrt{2\pi}\left|\frac{\sigma}{L}\right|\vartheta_3(\pi x/L, q)$$

Another aspect of the present invention is a Gaussian pulse PN LiDAR for differential absorption measurements. The Gaussian pulse PN LiDAR may utilize a LiDAR system 50 as shown in the blocked diagram of FIG. 12 except that the Gaussian pulse PN LiDAR does not require band pass filters 88 and 90. The Gaussian pulse PN LiDAR may otherwise be substantially identical to the system 50 of FIG. 12.

The Gaussian pulse LiDAR system transmits a periodic Gaussian pulse that is turned on and off in a very specific way based on a digital sequence with good auto correlation properties such as an ML-sequence, Barker code, etc. that have an amplitude from 0 to 1. The code is oversampled so that one bit extends over M samples. Each code bit is replaced by a Gaussian pulse, and this is what is transmitted through the LiDAR. A correlating kernel for that code is generated by taking that code, multiplying it by 2 and subtracting 1, then oversampling by a factor of q as before. Each bit of the correlating kernel is also replaced by Gaussian pulse that may or may not have the same width as the transmitted Gaussian pulses. An approximation of this system can be constructed as follows. Let PN be the digital sequence (some type of PN code) and PN be the oversampled PN code. The oversampled code is then:

$$PN(n)=pn(int((n-1/M)+1)) \tag{23.0}$$

where int is the integer part. We define a function W such that $$W(x,q)=\vartheta_3(\pi x,q)/\vartheta_3(0,q) \tag{24.0}$$

where $\vartheta_3$ is the Jacobi theta function of the third kind and q is the nome. By definition this function is derived as a sum of Gaussian pulses and q is related to the standard deviation of these pulse by, $$q=\exp(-2\pi^2\sigma^2) \tag{25.0}$$

where σ is the standard deviation of the Gaussian pulse.

To generate the outgoing pulses we write $$S_{out}(n)=PN(n)W((n-\tfrac{1}{2})/M-\tfrac{1}{2},q) \tag{26.0}$$

The correlating kernel is generated from $$K(n)=(2PN(n)-1)W((n-\tfrac{1}{2})/M-\tfrac{1}{2},q') \tag{27.0}$$

Where q' may or may not be the same as q. Choosing a different (usually smaller) value for q prime is useful in adjusting the shape of the autocorrelation function to make it more suitable for absorption measurements.

Figure 31:
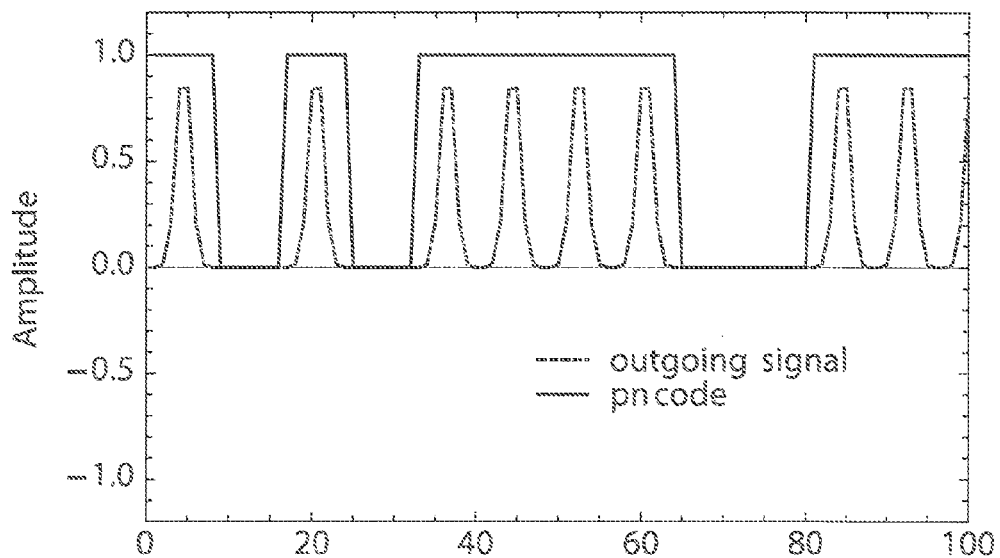
FIG. 31 is a plot of a PN code modulated by a Jacobi theta function of the third kind formed by multiplying the PN code by the theta function. This creates a pulse for each bit of the PN code and is used as the transmitted laser modulation signal.
Figure 32:
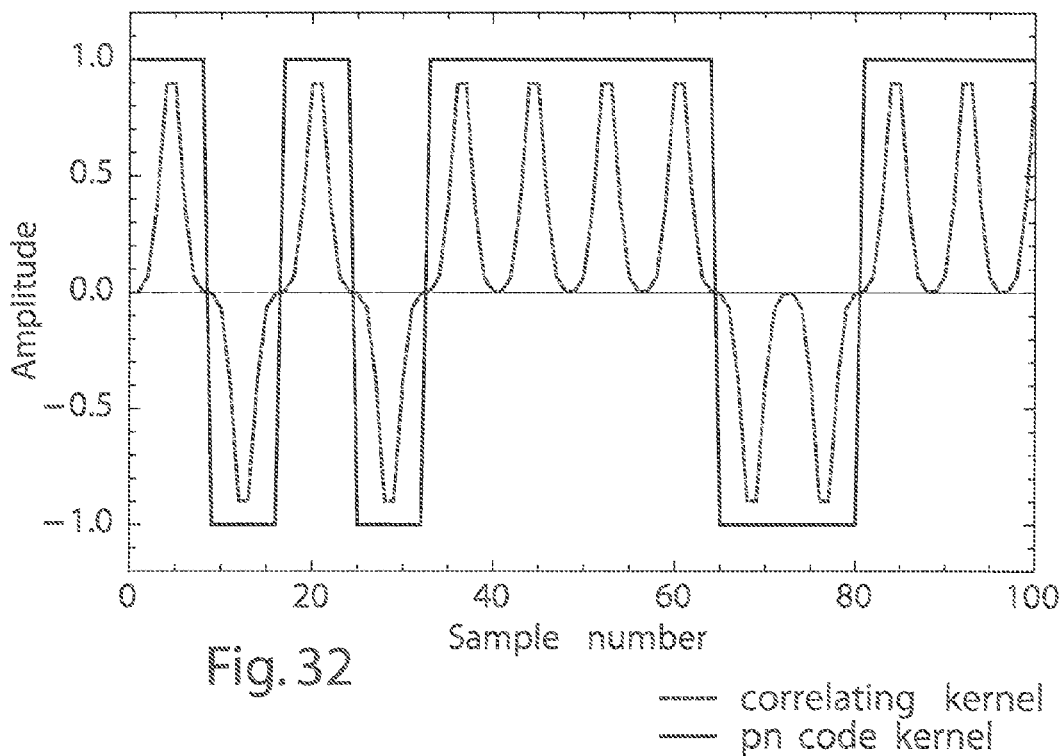
FIG. 32 is a plot showing an example of a correlating kernel formed by taking twice the PN code, subtracting 1, and multiplying the result by the Jacobi theta function of the third kind used in FIG. 31.
Figure 33:
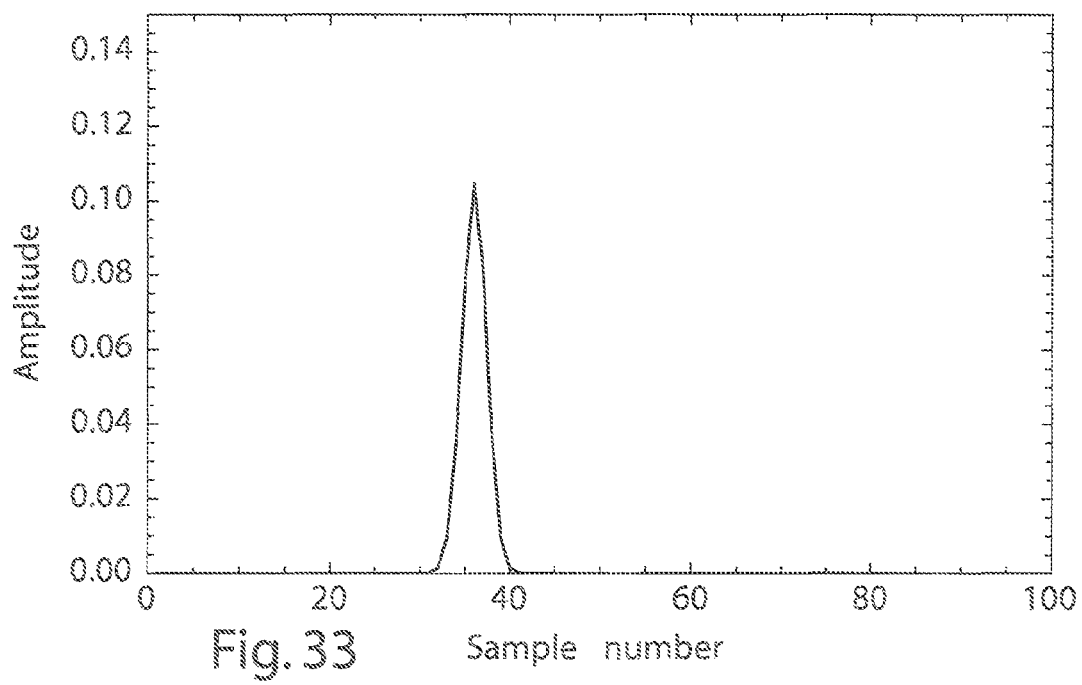
FIG. 33 is a plot of the resulting autocorrelation function for the theta function pulse-pn modulation.

An example plot of the outgoing signal is shown in FIG. 31. An example of the correlating kernel is shown in FIG. 32. The resulting cross correlation between the outgoing signal and correlating kernel is shown in FIG. 33.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A method of utilizing an intensity modulated laser beam to provide for measurement of differential absorption in a continuous wave lidar system, the method comprising:
   utilizing a laser to provide a first light beam having a first wavelength;
   utilizing a laser to provide a second light beam having a second wavelength that is not equal to the first wavelength;
   utilizing a PN code to provide a modulation signal having an intensity modulated (IM) repeating wave form corresponding to the PN code;
   providing intensity modulation of the first and second light beams whereby the first and second light beams comprise first and second transmitted signals corresponding to the modulation signal, wherein the first transmitted signal is time shifted relative to the second transmitted signal;
   directing the first and second light beams at a target such that at least a portion of the first light beam is reflected, and at least a portion of the second light beam is reflected;
   receiving at least a portion of the reflected first and second light beams to form a received signal;
   demodulating the received signal utilizing the modulation signal to provide first and second distinct amplitude peaks;
   determining a magnitude of the first amplitude peak;
   determining a magnitude of the second amplitude peak; and
   utilizing the magnitudes of the first and second peaks to determine a relative absorption of the first and second light beams.

2. The method of claim 1, wherein:
the IM repeating wave form comprises an amplitude modulated sine wave.

3. The method of claim 2, wherein:
the received signal is demodulated utilizing a quadrature matched filter correlator.

4. The method of claim 3, wherein:
the quadrature matched filter correlator provides a matched filter correlation utilizing a PN code kernel.

5. The method of claim 1, wherein:
the IM repeating waveform comprises a sine wave amplitude modulated by a PN code.

6. The method of claim 5, wherein:
the received signal is demodulated utilizing a quadrature matched filter correlator.

7. The method of claim 1, wherein:
the IM repeating wave form comprises a phase modulated sine wave.

8. The method of claim 7, wherein:
the received signal is demodulated utilizing a quadrature matched filter correlator.

9. The method of claim 1, wherein:
the IM repeating waveform comprises a PN code phase modulated sine wave.

10. The method of claim 9, wherein:
the received signal is demodulated utilizing a quadrature matched filter correlator.

11. The method of claim 1, wherein:
the IM repeating waveform comprises a frequency modulated sine wave.

12. The method of claim 11, wherein:
the received signal is demodulated utilizing a quadrature matched filter correlator.

13. The method of claim 1, wherein:
the IM repeating waveform comprises a PN code frequency modulated sine wave.

14. The method of claim 13, wherein:
the received signal is demodulated utilizing a quadrature matched filter correlator.

15. The method of claim 1, wherein:
the IM repeating waveform comprises a sine squared modulated PN code forming a single pulse for each bit of the PN code.

16. The method of claim 15, wherein:
the IM repeating waveform is demodulated using a correlating kernel formed from twice the PN code minus one.

17. The method of claim 15, wherein:
the IM repeating waveform is demodulated using a correlating kernel formed from twice the PN code minus one multiplied by a sine squared function forming a single pulse for each bit of the PN code.

18. The method of claim 1, wherein:
the IM repeating waveform comprises a repeating Gaussian pulse modulated PN code forming a single pulse for each bit of the PN code.

19. The method of claim 18, wherein:
the IM repeating waveform is demodulated using a correlating kernel formed from twice the PN code minus one.

20. The method of claim 18, wherein:
the IM repeating waveform is demodulated using a correlating kernel formed from twice the PN code minus one multiplied by a repeating Gaussian pulse forming a single pulse for each bit of the PN code.

21. The method of claim 1, wherein:
the IM repeating waveform comprises a Jacobi theta function of the third kind modulated PN code forming a single pulse for each bit of the PN code.

22. The method of claim 21, wherein:
the IM repeating waveform is demodulated using a correlating kernel formed from twice the PN code minus one.

23. The method of claim 21, wherein:
the IM repeating waveform is demodulated using a correlating kernel formed from twice the PN code minus one multiplied by a Jacobi function of the third forming a single pulse for each bit of the PN code.

24. The method of claim 21, wherein:
the IM repeating waveform is demodulated using a correlating kernel formed from twice the PN code minus one multiplied by a repeating analog pulse forming a single pulse for each bit of the PN code.

25. The method of claim 1, wherein:
the IM repeating waveform comprises an analog pulse modulated PN code forming a single pulse for each bit of the PN code.

26. The method of claim 25, wherein:
the IM repeating waveform is demodulated using a correlating kernel formed from twice the PN code minus one.

27. The method of claim 1, wherein:
the PN code is filtered utilizing a cyclic frequency attenuation function based on a Jacobi theta function of the third kind.
28. The method of claim 1, wherein:
the PN code comprises a filtered PN code.

* * * * *